(12) United States Patent
Desjarlais et al.

(10) Patent No.: US 9,266,966 B2
(45) Date of Patent: Feb. 23, 2016

(54) COMPOSITIONS AND METHODS FOR TREATING IGE-MEDIATED DISORDERS

(71) Applicant: Xencor, Inc., Monrovia, CA (US)

(72) Inventors: John Desjarlais, Pasadena, CA (US); Seung Y. Chu, Cypress, CA (US); Holly M. Horton, Boston, MA (US); Matthew J. Bernett, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 14/510,054

(22) Filed: Oct. 8, 2014

(65) Prior Publication Data

US 2015/0093379 A1     Apr. 2, 2015

Related U.S. Application Data

(60) Continuation of application No. 13/784,649, filed on Mar. 4, 2013, and a division of application No. 12/562,088, filed on Sep. 17, 2009, now Pat. No. 8,435,517.

(60) Provisional application No. 61/097,819, filed on Sep. 17, 2008.

(51) Int. Cl.
  *A61K 39/395* (2006.01)
  *C07K 16/42* (2006.01)
  *C07K 16/46* (2006.01)

(52) U.S. Cl.
  CPC ........... *C07K 16/4291* (2013.01); *C07K 16/464* (2013.01); *C07K 2317/24* (2013.01); *C07K 2317/52* (2013.01); *C07K 2317/732* (2013.01); *C07K 2317/76* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 5,091,313 A | 2/1992 | Chang et al. | |
| 5,342,924 A | 8/1994 | Chang et al. | |
| 5,449,760 A | 9/1995 | Chang et al. | |
| 5,543,144 A | 8/1996 | Chang et al. | |
| 5,614,611 A | 3/1997 | Chang et al. | |
| 5,693,762 A | 12/1997 | Queen et al. | |
| 5,958,708 A * | 9/1999 | Hardman et al. | 435/7.21 |
| 6,037,453 A | 3/2000 | Jardieu et al. | |
| 6,066,718 A | 5/2000 | Hardman et al. | |
| 6,072,035 A | 6/2000 | Hardman et al. | |
| 6,329,509 B1 | 12/2001 | Jardieu et al. | |
| 6,602,684 B1 | 8/2003 | Umana et al. | |
| 6,761,889 B2 | 7/2004 | Lowman et al. | |
| 6,797,492 B2 | 9/2004 | Daugherty et al. | |
| 7,117,096 B2 | 10/2006 | Luo et al. | |
| 7,118,743 B2 | 10/2006 | Thomas et al. | |
| 7,317,091 B2 | 1/2008 | Lazar et al. | |
| 7,655,229 B2 | 2/2010 | Chan et al. | |
| 7,662,925 B2 | 2/2010 | Lazar et al. | |
| 8,039,592 B2 | 10/2011 | Lazar et al. | |
| 8,063,187 B2 | 11/2011 | Chu et al. | |
| 8,084,582 B2 | 12/2011 | Dahiyat et al. | |
| 8,093,357 B2 | 1/2012 | Lazar et al. | |
| 8,093,359 B2 | 1/2012 | Lazar et al. | |
| 8,101,720 B2 | 1/2012 | Lazar et al. | |
| 8,124,731 B2 | 2/2012 | Lazar et al. | |
| 8,188,231 B2 | 5/2012 | Lazar et al. | |
| 8,435,517 B2 * | 5/2013 | Desjarlais et al. | 424/133.1 |
| 2001/0038839 A1 * | 11/2001 | Jardieu et al. | 424/130.1 |
| 2002/0119492 A1 | 8/2002 | Chirino et al. | |
| 2003/0003097 A1 | 1/2003 | Reff et al. | |
| 2003/0157108 A1 | 8/2003 | Presta et al. | |
| 2004/0197326 A1 * | 10/2004 | Fick et al. | 424/131.1 |
| 2004/0230380 A1 | 11/2004 | Chirino et al. | |
| 2005/0249723 A1 | 11/2005 | Lazar et al. | |
| 2006/0008883 A1 | 1/2006 | Lazar et al. | |
| 2006/0024298 A1 | 2/2006 | Lazar et al. | |
| 2006/0148009 A1 | 7/2006 | Barbosa et al. | |
| 2007/0004909 A1 | 1/2007 | Johnson et al. | |
| 2007/0231329 A1 | 10/2007 | Lazar et al. | |
| 2007/0248602 A1 | 10/2007 | Lazar et al. | |
| 2008/0003218 A1 | 1/2008 | Lowman et al. | |
| 2008/0154025 A1 | 6/2008 | Lazar et al. | |
| 2008/0181890 A1 * | 7/2008 | Lazar et al. | 424/133.1 |
| 2009/0060910 A1 | 3/2009 | Johnson et al. | |
| 2009/0136485 A1 | 5/2009 | Chu et al. | |
| 2010/0174053 A1 | 7/2010 | Johnson et al. | |
| 2010/0249382 A1 | 9/2010 | Desjarlais et al. | |

(Continued)

FOREIGN PATENT DOCUMENTS

JP    2008-513351    5/2008
WO    WO 92-11018    7/1992

(Continued)

OTHER PUBLICATIONS

Allen et al. "Modifications to an Fcγ-Fcε fusion protein after its effectivenes in the inhibition of FcεRI-mediated functions" *J. Allergy Clin. Immunol.* (2007) 120(2):462-468.
Anderson et al., 2004, "An expanded genetic code with a functional quadruplet codon" Proc. Natl. Acad. Sci. U.S.A. 101(2):7566-71.
Arbes et al., Prevalences of positive skin test responses to 10 common allergens in the US population: Results from the Third National Health and Nutrition Examination Survey, Clinical Gastroenterology 116(2), 377-383 (2005).
Ashkenazi et al., "Immunoadhesins as research tools and therapeutic agents" 1997, Curr Opin Immunol 9:195-200.
Bitonti et al. "Pulmonary delivery of an erythropoietin Fc fusion protein in non-human primates through an immunoglobulin transport pathway" (2004) Proc. Nat. Acad. Sci. 101:9763-8.
Bruggemann et al., "Regulation of the flavin redox potential by flavin-binding antibodies" 1997, Curr Opin Biotechnol 8:455-458.
Caramori et al., "New drugs targeting Th2 lymphocytes in asthma" 2008, Journal of Occupational Medicine and Toxicology 3-S1-S6.
Carter, et al, "Potent antibody therapeutics by design" 2006, Nature Reviews Immunology 6:343-357.

(Continued)

*Primary Examiner* — Michael Szperka
(74) *Attorney, Agent, or Firm* — Robin M. Silva; Louis T. Nguyen; Morgan, Lewis & Bockius, LLP

(57) ABSTRACT

The present invention relates to immunoglobulins that bind IgE and FcγRIIb with high affinity, said compositions being capable of inhibiting cells that express membrane-anchored IgE. Such compositions are useful for treating IgE-mediated disorders, including allergies and asthma.

1 Claim, 13 Drawing Sheets

(56) References Cited

U.S. PATENT DOCUMENTS

| | | |
|---|---|---|
| 2011/0021755 A1 | 1/2011 | Lazar et al. |
| 2011/0250681 A1 | 10/2011 | Lazar et al. |
| 2012/0148578 A1 | 6/2012 | Chu et al. |
| 2012/0156207 A1 | 6/2012 | Chu et al. |
| 2012/0156220 A1 | 6/2012 | Chu et al. |
| 2014/0212435 A1 | 7/2014 | Moore et al. |

FOREIGN PATENT DOCUMENTS

| | | |
|---|---|---|
| WO | WO 00-61739 | 10/2000 |
| WO | WO 01-29246 | 4/2001 |
| WO | WO 02-30954 | 4/2002 |
| WO | WO 02-31140 | 4/2002 |
| WO | WO 2004-004798 | 1/2004 |
| WO | WO 2004-070011 | 8/2004 |
| WO | WO 2006-048781 | 5/2006 |
| WO | WO 2007-044616 | 7/2007 |
| WO | WO 2009-086320 | 7/2009 |
| WO | WO 2009-129538 | 10/2009 |

OTHER PUBLICATIONS

Chamow et al., "Immunoadhesins: principles and applications" 1996, Trends Biotechnol 14:52-60.

Chin et al., "An Expanded Eukaryotic Genetic Code" 2003, Science 301(5635):964-7.

Chu, S. et al., "Inhibition of B cell receptor-mediated activation of primary human B cells by coengagement of CD19 and FcgammaRIIb with Fc-engineered antibodies." 2008 *Molecular Immunology*, vol. 45, No. 15, 3926-3933.

Clark, "IgG effector mechanisms", 1997,Chem Immunol. 65:88-110.

Corne, J et al., "The Effect of Intravenous Administration of a Chimeric Anti-IgE Antibody on Serum IgE Levels in Atopic Subjects: Efficacy, Safety, and Pharmacokinetics" 1997, J Clin Invest 99:879-887.

Cox et al., "Glycan optimization of a human monoclonal antibody in the aquatic plant Lemna minor" 2006, Nat Biotechnol 24(12):1591-7.

Cropp & Shultz,"An expanding genetic code" 2004, Trends Genet. 20(12):625-30.

Dall'Acqua et al. "Increasing the Affinity of a Human IgG1 for the Neonatal Fc Receptor: Biological Consequences1" Journal of Immunology, 2002, 169:5171-5180.

Dall'Acqua et al., "Properties of Human IgG1s Engineered for Enhanced Binding to the Neonatal Fc Receptor (FcRn)" 2006, The Journal of biological chemistry 281:23514-23524.

Davies et al., "Expression of GnTIII in a Recombinant Anti-CD20 CHO Production Cell Line: Expression of Antibodies with Altered Glycoforms Leads to an Increase in ADCC Through Higher Affinity for FcγRIII" 2001, Biotechnol Bioeng 74:288-294.

Davis et al., "Fc receptor homologs: newest members of a remarkably diverse Fc receptor gene family" 2002, Immunol. Reviews 190:123-136.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody" 2002, J. Immunol. 169:3076-3084.

Edelman et al., "The Covalent Structure of an Entire γG Immunoglobulin Molecule" 1969, Proc Natl Acad Sci USA 63:78-85.

Ghetie et al., "Multiple Roles for the Major Histocompatibility Complex Class I—Related Receptor FCRN" 2000, Annu Rev Immunol 18:739-766.

Gorman & Clark, "Humanisation of monoclonal antibodies for the therapy" 1990, Semin Immunol 2(6):457-66.

Griffiths et al., "Strategies for selection of antibodies by phage display" 1998, Curr Opin Biotechnol 9:102-108.

Hayhurst & Georgiou, "High-throughput antibody isolation" 2001, *Curr Opin Chem Biol* 5:683-689.

Hinton et al. "An Engineered Human IgG1 Antibody with Longer Serum Half-Life" 2006 Journal of Immunology 176:346-356.

Hinton et al., "Engineered Human IgG Antibodies with Longer Serum Half-lives in Primates" 2004, J. Biol. Chem. 279(8): 6213-6216.

Holliger & Hudson, "Engineered antibody fragments and the rise of single domains" 2006, Nature Biotechnology 23(9):1126-1136.

Hubbard et al. "Synthesis and Processing of Asparagine-Linked Oligosaccharides1" 1981, Ann. Rev. Biochem. 50:555-583.

Infuhr et al., Allergy, 2005, 60:977-985.

Janeway, et al., Immunology, $3^{rd}$. Edition, 1997, Garland Press, pp. 3:1-3:11.

Jefferis et al., "IgG-Fc-mediated effector functions: molecular definition of interaction sites for effector ligands and the role of glycosylation" 1998, Immunol. Rev. 163:59-76.

Jefferis et al., "Interaction sites on human IgG-Fc for FcgR: current models" 2002, *Immunol Lett* 82:57-65.

Jones, "Replacing the complementarity-determining regions in a human antibody with those from a mouse" 1986, Nature 321:522-525.

Kaneko et al., "Anti-Inflammatory Activity of Immunoglobulin G Resulting from Fc Sialylation" 2006, Science 313:670-673.

Kim et al., "Analysis of FcgRIII and IgG Fc Polymorphism Reveals Functional and Evolutionary Implications of Protein—Protein Interaction" 2001, J. Mol. Evol. 54:1-9.

Kolbinger, F et al., "Humanization of a mouse anti-human IgE antibody: a potential therapeutic for IgE-mediated allergies " 1993, Protein Eng 6:971-980.

Lazar et al., 2007, Mol Immunol 44:1986-1998.

Lefranc, et al., The human IgG subclasses: molecular analysis of structure, function and regulation. Pergamon, Oxford, pp. 43-78 (1990).

Lefranc, G. et al., "Gm, Am and Km Immunoglobulin Allotypes of Two Populations in Tunisia" 1979, Hum. Genet.: 50, 199-211.

Li et al., "Optimization of humanized IgGs in glycoengineered Pichia Pastoris" 2006, Nature Biotechnology 24(2):210-215.

Lifely et al., "Glycosylation and biological activity of CAMPATH-1H expressed in different cell lines and grown under different culture conditions" 1995, Glycobiology 5(8): 813-822).

Loghem E van, "Allotypic markers", 1986, Monogr Allergy 19: 40-51.

Lowman et al., "Selecting High-Affinity Binding Proteins by Monovalen Phage Display" 1991, *Biochemistry* 30:10832-10838.

Maynard & Georgiou, "Antibody Engineering" 2000, *Annu Rev Biomed Eng* 2:339-76.

Mechetina et al., "Identification of CD16-2, a novel mouse receptor homologous to CD16/FcγRIII" *Immunogenetics*, 2002 54:463-468.

Mimura et al., "Role of Oligosaccharide Residues of IgG1-Fc in Fc_RIIb Binding " 2001, J Biol Chem 276:45539-45547.

Morea et al., "Antibody Modeling: Implications for Engineering and Design " 2000, Methods 20:267-279.

Morea et al., "Antibody structure, prediction and redesign" 1997, Biophys Chem 68:9-16.

Nechansky et al., 2007, Mol Immunjol 44(7):1826-8.

Paul, M.D., William, editor; Fundamental Immunology, 3d ed. Raven Press, 1993, p. 242.

Penichet et al., "Antibody—cytokine fusion proteins for the therapy of cancer " 2001, J. Immunol. Methods 248:91-101.

Portolano, et al., J. Immunol. Feb. 1, 1993; 150(3):880-887.

Presta, LG et al., "Humanization of an antibody directed against IgE" 1993, J Immunol 151:2623-2632.

Racine-Poon, A et al., "Efficacy, pharmacodynamics, and pharmacokinectics of CGP 51901, an anti-immunoglobulin E chimeric monoclonal antibody, in patients with seasonal allergic rhinitis" 1997, Clin Pharmcol Ther 62:675-690.

Radaev et al., "Recognition of IgG by Fcg Receptor" 2001, J Biol Chem 276:16478-16483.

Raghavan et al., "Fc Receptors and Their Interactions With Immunoglobulins" 1996, Annu Rev Cell Dev Biol 12:181-220.

Ravetch et al., "IGG Fc Receptors" 2001, Annu Rev Immunol 19:275-290.

(56) References Cited

OTHER PUBLICATIONS

Roguska et al., "Humanization of Murine Monoclonal Antibodies Through Variable Domain Resurfacing" 1994, Proc. Natl. Acad. Sci. USA 91:969-973.
Roque et al.,"Antibodies and Genetically Engineered Related Molecules: Production and Purification" 2004, Biotechnol. Prog. 20:639-654.
Rudikoff et al., PNAS, Mar. 1982; 79(6):1979-1983.
Saxon et al., "Accenutate the negative, eliminate the positive": Engineering allergy therapeutics to block allergic reactivity through negative signaling. 2008 *J. of Allergy and Clinical Immunology*, vol. 121, No. 2, 320-325.
Scallon et al., "Higher levels of sialylated Fc glycans in immunoglobulin G molecules can adversely impact functionality" 2007, Mol Immunol. 44(7):1524-34.
Shields et al., "High Resolution Mapping of the Binding Site on Human IgG1 for FcgRI, FcgRII, FcgRIII, and FcRn and Design of IgG1 Variants with Improved Binding to the FcgR" 2001, J Biol Chem 276:6591-6604.
Shields et al., "Lack of Fucose on Human IgG1 N-Linked Oligosaccharide Improves Binding to Human Fc_RIII and Antibody-dependent Cellular Toxicity" 2002, J Biol Chem 277:26733-26740.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity" 2003, J Biol Chem 278:3466-3473).
Simmons et al., "Expression of full-length immunoglobulins in *Escherichia coli*: rapid and efficient production of aglycosylated antibodies " 2002, J Immunol Methods 263:133-147.
Smith, "Filamentous Fusion Phage: Novel Expression Vectors That Display Cloned Antigens on the Virion Surface "1985, *Science* 228:1315-1317.
Sondermann et al., "Molecular Basis for Immune Complex Recognition: A Comparison of Fc-Receptor Structures" 2001, J Mol Biol 309:737-749.
Sondermann et al., "The 3.2-AÊ crystal structure of the human IgG1 Fc fragment±FcgRIII complex" 2000, Nature 406:267-273.
Stanley et al., "A Dominant Mutation to Ricin Resistance in Chinese Hamster Ovary Cells Induces UDP-G1cNAc:Glycopeptide,8-4-N-Acetylglucosaminyltransferasl1e1 Activity" 1984, J. Biol. Chem. 261:13370-13378).
Su et al., "Expression Profile of FcγRIIb on Leukocytes and its dysregulation in systemic lupus erythematosus" *Journ of Immunol.* (2007) 178:3272-3280.
Tan et al., ""Superhumanized" Antibodies: Reduction of Immunogenic Potential by Complementarity-Determining Region Grafting with Human Germline Sequences: Application to an Anti-CD281" 2002, J. Immunol. 169:1119-1125.
Trail et al., "Monoclonal antibody drug conjugates in the treatment of cancer" 1999, Curr. Opin. Immunol. 11:584-588.
Tsurushita & Vasquez, "Humanization of Monoclonal Antibodies, Molecular Biology of B Cells," 2004, 533-545.
Umana et al., "Engineered glycoforms of an antineuroblastoma IgG1 with optimized antibodydependent cellular cytotoxic activity" 1999, Nature Biotech. 17:176-180.
Verhoeyen et al., "Reshaping Human Antibodies: Grafting anAntilysozyme Activity" 1988, Science 239:1534-1536.
Veri et al. "Monoclonoal antibodies capable of discriminationg the human inhibitory Fcγ-receptor IIb (CD32B) from the activiting Fcγ-receptor IIA (CD32A): biochemical, biological and functional characterization" *Blackwell Pub. Ltd. Immunol.* (2007) 121:392-404.
WHO Review of the notation for the allotypic and related markers of human immunoglobulins. 1976, Eur. J. Immunol. 6, 599-601.
WHO Review of the notation for the allotypic and related markers of human immunoglobulins. J Immunogen 1976, 3: 357-362.
Wiggington, S. et al., "an immunoglobulin E-reactive chimeric human immunoglobulin G1 anti-idiotype inhibits basophil degranulation through cross-linking of Fcepsilon RI with FcgammaRIIb" 2007, *Clinical and Experimental Allergy* vol. 38, No. 2, 313-319.
Wiliam E. Paul, M.D., Fundamental Immunology, 3d ed. Raven Press, 1993, p. 242.
Wright et al., Effect of glycosylation on "antibody function: implications for genetic engineering " 1997, Trends Biotech 15:26-32.
Zhang et al., "A New Strategy for the Synthesis of Glycoproteins" 2003,:371-3.
Bang et al., Spotlight on omalizumab in allergic asthma., BioDrugs. 2004;18(6):415-8.

\* cited by examiner

Figure 4

| Antibody | FcγRI KD (M) | Fold | H131 FcγRIIa KD (M) | Fold | FcγRIIb KD (M) | Fold | V158 FcγRIIIa KD (M) | Fold |
|---|---|---|---|---|---|---|---|---|
| Native IgG1 | 2.8E-10 | 1.0 | 8.5E-07 | 1.0 | 1.8E-06 | 1.0 | 2.0E-07 | 1.0 |
| S267E | 2.6E-10 | 1.1 | 9.6E-07 | 0.89 | 6.0E-08 | 30 | 6.9E-07 | 0.29 |
| G236D/S267E | 3.2E-09 | 0.088 | 2.2E-06 | 0.39 | 2.5E-08 | 72 | n.d. | |
| S239D/S267E | 1.7E-10 | 1.6 | 7.0E-07 | 1.2 | 1.2E-08 | 150 | 6.2E-08 | 3 |
| S267E/L328F | 2.3E-10 | 1.2 | 8.8E-07 | 0.97 | 4.2E-09 | 429 | n.d. | |
| S239D/I332E | 1.4E-10 | 2.0 | 2.2E-07 | 3.9 | 8.8E-08 | 20 | 6.8E-09 | 29 |
| G236R/L328R | n.d. | | n.d. | | n.d. | | n.d. | |

Figure 5

Omalizumab VH (SEQ ID NO:1)

EVQLVESGGGLVQPGGSLRLSCAVSGYSITSGYSWNWIRQAPGKGLEWVASITYDGSTNY
NPSVKGRITISRDDSKNTFYLQMNSLRAEDTAVYYCARGSHYFGHWHFAVWGQGTLVTVS
S

Omalizumab VH CDR1 (SEQ ID NO:2)

YSITSGYSW

Omalizumab VH CDR2 (SEQ ID NO:3)

TYDGS

Omalizumab VH CDR3 (SEQ ID NO:4)

GSHYFGHWHFAV

Omalizumab VL (SEQ ID NO:5)

DIQLTQSPSSLSASVGDRVTITCRASQSVDYDGDSYMNWYQQKPGKAPKLLIYAASYLESG
VPSRFSGSGSGTDFTLTISSLQPEDFATYYCQQSHEDPYTFGQGTKVEIK

Omalizumab VL CDR1 (SEQ ID NO:6)

QSVDYDGDSY

Omalizumab VL CDR2 (SEQ ID NO:7)

AASYLES

Omalizumab VL CDR3 (SEQ ID NO:8)

SHEDPYT

MaE11 VH (SEQ ID NO:9)

DVQLQESGPGLVKPSQSLSLACSVTGYSITSGYSWNWIRQFPGNKLEWMGSITYDGSSNY
NPSLKNRISVTRDTSQNQFFLKLNSATAEDTATYYCARGSHYFGHWHFAVWGAGTTVTVS
S

MaE11 VH CDR1 (SEQ ID NO:10)

YSITSGYSW

MaE11 VH CDR2 (SEQ ID NO:11)

TYDGS

Figure 5 (continued)

MaE11 VH CDR3 (SEQ ID NO:12)

GSHYFGHWHFAV

MaE11 VL (SEQ ID NO:13)

DIQLTQSPASLAVSLGQRATISCKASQSVDYDGDSYMNWYQQKPGQPPILLIYAASYLGSEI
PARFSGSGSGTDFTLNIHPVEEEDAATFYCQQSHEDPYTFGAGTKLEIK

MaE11 VL CDR1 (SEQ ID NO:14)

QSVDYDGDSY

MaE11 VL CDR2 (SEQ ID NO:15)

AASYLGS

MaE11 VL CDR3 (SEQ ID NO:16)

SHEDPYT

H1L1MaE11 VH (SEQ ID NO:17)

QVQLQESGPGLVKPSETLSLTCAVSGYSITSGYSWNWIRQPPGKKLEWIGSITYDGSSNYNPSLKSRVTIS
RDTSKNQFSLKLSSVTAADTAVYYCARGSHYFGHWHFAVWGAGTLVTVSS

H1L1 MaE11 VH CDR1 (SEQ ID NO:18)

YSITSGYSW

H1L1 MaE11 VH CDR2 (SEQ ID NO:19)

TYDGS

H1L1 MaE11 VH CDR3 (SEQ ID NO:20)

GSHYFGHWHFAV

H1L1 MaE11 VL (SEQ ID NO:21)

DIQLTQSPSSLSASVGDRVTITCRASQSVDYDGDSYMNWYQQKPGQPPKLLIYAASYLGSE
IPARFSGSGSGTDFTLTISSLQPEDFATYYCQQSHEDPYTFGAGTKLEIK

H1L1 MaE11 VL CDR1 (SEQ ID NO:22)

QSVDYDGDSY

H1L1 MaE11 VL CDR2 (SEQ ID NO:23)

AASYLGS

H1L1 MaE11 VL CDR3 (SEQ ID NO:24)

SHEDPYT

TES-C21 VH (SEQ ID NO:25)

QVQLQQSGAELMKPGASVKISCKTTGYTFSMYWLEWVKQRPGHGLEWVGEISPGTFTTN
YNEKFKAKATFTADTSSNTAYLQLSGLTSEDSAVYFCARFSHFSGSNYDYFDYWGQGTSLT
VSS

TES-C21 VH CDR1 (SEQ ID NO:26)

YTFSMYW

TES-C21 VH CDR2 (SEQ ID NO:27)

SPGTFT

Figure 5 (continued)

TES-C21 VH CDR3 (SEQ ID NO:28)

FSHFSGSNYDYFDY

TES-C21 VL (SEQ ID NO:29)

DILLTQSPAILSVSPGERVSFSCRASQSIGTNIHWYQQRTDGSPRLLIKYASESISGIPSRFSG
SGSGTEFTLNINSVESEDIADYYCQQSDSWPTTFGGGTKLEIK

TES-C21 VL CDR1 (SEQ ID NO:30)

QSIGTN

TES-C21 VL CDR2 (SEQ ID NO:31)

YASESIS

TES-C21 VL CDR3 (SEQ ID NO:32)

SDSWPTT

Figure 6

Ckappa light chain (SEQ ID NO:33)

RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Native IgG1 constant chain (SEQ ID NO:34)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

S267E/L328F IgG1 constant chain (SEQ ID NO:35)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKAFPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

G236D/S267E IgG1 constant chain (SEQ ID NO:36)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLDGPS
VFLFPPKPKDTLMISRTPEVTCVVVDVEHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

Figure 7

Omalizumab light chain (VH-Cκ) (SEQ ID NO:37)

DIQLTQSPSSLSASVGDRVTITCRASQSVDYDGDSYMNWYQQKPGKAPKLLIYAASYLESG
VPSRFSGSGSGTDFTLTISSLQPEDFATYYCQQSHEDPYTFGQGTKVEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

Omalizumab IgG1 heavy chain (SEQ ID NO:38)

EVQLVESGGGLVQPGGSLRLSCAVSGYSITSGYSWNWIRQAPGKGLEWVASITYDGSTNY
NPSVKGRITISRDDSKNTFYLQMNSLRAEDTAVYYCARGSHYFGHWHFAVWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK

Omalizumab S267E/L328F heavy chain (SEQ ID NO:39)

EVQLVESGGGLVQPGGSLRLSCAVSGYSITSGYSWNWIRQAPGKGLEWVASITYDGSTNY
NPSVKGRITISRDDSKNTFYLQMNSLRAEDTAVYYCARGSHYFGHWHFAVWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGP
SVFLFPPKPKDTLMISRTPEVTCVVVDVEHEDPEVKFNWYVDGVEVHNAKTKPREEQYNST
YRVVSVLTVLHQDWLNGKEYKCKVSNKAFPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK

H1L1 MaE11 light chain (VH-Cκ) (SEQ ID NO:40)

DIQLTQSPSSLSASVGDRVTITCRASQSVDYDGDSYMNWYQQKPGQPPKLLIYAASYLGSE
IPARFSGSGSGTDFTLTISSLQPEDFATYYCQQSHEDPYTFGAGTKLEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

H1L1 MaE11 IgG1 heavy chain (SEQ ID NO:41)

QVQLQESGPGLVKPSETLSLTCAVSGYSITSGYSWNWIRQPPGKKLEWIGSITYDGSSNYNPSLKSRVTIS
RDTSKNQFSLKLSSVTAADTAVYYCARGSHYFGHWHFAVWGAGTLVTVSSASTKGPSVFPLAPSSKS
TSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYT
QKSLSLSPGK

H1L1 MaE11 S267E/L328F heavy chain (SEQ ID NO:42)

QVQLQESGPGLVKPSETLSLTCAVSGYSITSGYSWNWIRQPPGKKLEWIGSITYDGSSNYNPSLKSRVTIS
RDTSKNQFSLKLSSVTAADTAVYYCARGSHYFGHWHFAVWGAGTLVTVSSASTKGPSVFPLAPSSKS
TSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTP
EVTCVVVDVEHEDPEVKFNWYVDGVEVHNAKTKPREEQYNSTYRVVSVLTVLHQDWLNG
KEYKCKVSNKAFPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYT
QKSLSLSPGK

| Antibody | IgE KD (M) | FcγRIIb KD (M) | FcγRIIb Fold |
|---|---|---|---|
| Omalizumab_IgG1_WT | 2.2E-10 | 1.94E-06 | 1.0 |
| Omalizumab_IgG1_S267E/L328F | 2.0E-10 | 1.4E-08 | 135 |
| MaE11_H1L1_IgG1_WT | 6.1E-11 | 2.0E-06 | 1.0 |
| MaE11_H1L1_IgG1_S267E/L328F | 6.3E-11 | 5.6E-09 | 366 |
| MaE11_H1L1_IgG1_G236R/L328R | 6.4E-11 | NB | |

COMPOSITIONS AND METHODS FOR TREATING IGE-MEDIATED DISORDERS

CROSS-REFERENCE TO RELATED APPLICATIONS

This application is a continuation of U.S. application Ser. No. 13/784,649, filed Mar. 4, 2013. This application is also a divisional of U.S. application Ser. No. 12/562,088, filed Sep. 17, 2009, now U.S. Pat. No. 8,435,517, which claims the benefit of U.S. Provisional Application Ser. No. 61/097,819, filed Sep. 17, 2008 under 35 U.S.C. 119(e) herein incorporated by reference in its entirety.

INCORPORATION OF RELATED APPLICATIONS

U.S. application Ser. No. 12/156,183, filed May 30, 2008, entitled "Methods and Compositions for Inhibiting CD32b Expressing cells", is herein incorporated by reference in its entirety.

TECHNICAL FIELD

The present disclosure relates to immunoglobulin compositions that bind IgE and FcγRIIb with high affinity, said compositions being capable of inhibiting cells that express membrane-anchored IgE. Such compositions are useful for treating IgE-mediated disorders, including allergies and asthma.

BACKGROUND OF THE INVENTION

Allergic diseases and conditions, such as asthma, allergic rhinitis, atopic dermatitis, and food allergy, have become increasingly prevalent over the past few decades and now affect 10-40% of the population in industrialized countries. Allergic diseases profoundly affect the quality of life, and can result in serious complications, including death, as may occur in serious cases of asthma and anaphylaxis. Allergies are prevalent, and are the largest cause of time lost from work and school and their impact on personal lives as well as their direct and indirect costs to the medical systems and economy are enormous. For example, allergic rhinitis (hay fever) affects 22% or more of the population of the USA, whereas allergic asthma is thought to affect at least 20 million residents of the USA. The economic impact of allergic diseases in the United States, including health care costs and lost productivity, has been estimated to amount to $6.4 billion in the early nineties alone.

Most allergic diseases are caused by immunoglobulin E (IgE)-mediated hypersensitivity reactions. IgE is a class of antibody normally present in the serum at minute concentrations. It is produced by IgE-secreting plasma cells that express the antibody on their surface at a certain stage of their maturation. Allergic patients produce elevated levels of IgE with binding specificity for ordinarily innocuous antigens to which they are sensitive. These IgE molecules circulate in the blood and bind to IgE-specific receptors on the surface of basophils in the circulation and mast cells along mucosal linings and underneath the skin. Binding of antigen or allergen to IgE on mast cells, basophils, and other cell types, crosslink the IgE molecules, and aggregate the underlying receptors, thus triggering the cells to release vasoactive and neuronal stimulatory mediators such as histamines, leukotrienes, prostaglandins, bradykinin, and platelet-activating factor. The rapid reaction of the immune system to antigen caused by antibody immune complexes has led to the term immediate or antibody-mediated hypersensitivity reaction, in contrast to delayed or cell-mediated hypersensitivity reactions that are mediated by T cells. IgE-mediated immune reactions are specifically referred to as type I hypersensitivity reactions.

The high affinity receptor for IgE (FcεRI) is a key mediator for immediate allergic manifestations. In addition to mast cells and basophils, the primary mediators of allergic reactions, FcεRI is found on a number of other cell types including eosinophils, platelets and on antigen-presenting cells such as monocytes and dendritic cells. An additional receptor for IgE is FcεRII, also known as CD23 or the low-affinity IgE Fc receptor. FcεRII is expressed broadly on B lymphocytes, macrophages, platelets, and many other cell types such as airway smooth muscle. FcεRII may play a role in the feedback regulation of IgE expression and subsequently FcεRII surface expression.

Since IgE plays a central role in mediating most allergic reactions, devising treatments to control IgE levels in the body and regulating IgE synthesis has been of great interest. Several strategies have been proposed to treat IgE-mediated allergic diseases by downregulating IgE levels. One strategy involves neutralizing the IgE molecules by binding the ε-chain of IgE in or near the Fc-receptor binding site. For example, Omalizumab (Xolair) is a recombinant humanized monoclonal anti-IgE antibody that binds to IgE on the same Fc site as FcεRI. Omalizumab causes a reduction in total serum or circulating IgE in atopic patients, which attenuates the amount of antigen-specific IgE that can bind to and sensitize tissue mast cells and basophils. This, in turn, leads to a decrease in symptoms of allergic diseases. Interestingly, serum IgE levels increase after start of therapy because of omalizumab-IgE complex formation and may remain high up to a year after stopping therapy. Consequently, this issue may lead to false-negatives on diagnostic tests and therefore IgE levels must be routinely checked. Accordingly, there exists a need for improved methods and compositions to reduce IgE-mediated diseases and disease symptoms.

SUMMARY OF EXEMPLARY EMBODIMENTS

The present disclosure provides novel coengagement molecules that bind IgE and FcγRIIb with high affinity, compositions comprising such coengagement molecules, and methods of using said novel coengagement molecules to treat IgE-mediated disorders. The coengagement molecules of the invention are capable of inhibiting cells that express membrane IgE and FcγRIIb, i.e. IgE+ FcγRIIb+ cells. The coengagement molecules of the invention are also preferably capable of binding circulating IgE. The inhibitory methods disclosed herein comprise contacting IgE+ FcγRIIb+ cells with a coengagement molecule that coengages IgE and FcγRIIb on the cell's surface.

The compositions disclosed herein include coengagement molecules capable of coengagement of IgE and FcγRIIb with high affinity on the cell's surface. In one embodiment the coengagement molecule includes an immunoglobulin that binds IgE and FcγRIIb with high affinity. The coengagement molecules of the invention preferably coengage membrane-anchored IgE and FcγRIIb on a cell's surface and preferably bind FcγRIIb with a Kd of less than about 100 nM. In a preferred embodiment the coengagement molecule is an immunoglobulin and in an additional preferred embodiment, the immunoglobulin is an antibody, wherein the Fv region of said antibody specifically binds IgE. In a preferred embodiment, said antibody binds both circulating and membrane-anchored IgE. In alternate embodiments, said antibody selectively binds membrane-anchored IgE relative to circulating IgE. In another embodiment, the coengagement molecule is a bispecific antibody having a first target specific region and a second target specific region, wherein the first target specific region binds IgE and the second target specific region binds FcγRIIb with a Kd of less than about 100 nM. In a preferred embodiment the first and second target specific regions are Fv regions, wherein the first Fv region binds IgE, and the second Fv region binds FcγRIIb with a Kd of less than about 100 nM. In another embodiment, coengagement molecule is an Fc fusion comprising an Fc region, wherein said Fc region binds FcγRIIb with a Kd of less than about 100 nM. In this embodiment, the Fc fusion partner of the immunoglobulin binds IgE.

In one embodiment, the coengagement molecule binds with FcγRIIb, wherein the affinity of said binding has a Kd less than about 100 nM, e.g., less than or equal to about 95 nM, less than or equal to about 90 nM, less than or equal to about 85 nM, less than or equal to about 80 nM, less than or equal to about 75 nM, less than or equal to about 74 nM.

In one embodiment, the coengagement molecule that coengages IgE and FcγRIIb with high affinity includes a variant immunoglobulin relative to a parent immunoglobulin. In one embodiment, the variant immunoglobulin comprises a variant Fc region, wherein said variant Fc region comprises one or more (e.g., two or more) modification(s) compared to a parent Fc region, wherein said modification(s) are at positions selected from the group consisting of 234, 235, 236, 237, 239, 265, 266, 267, 268, 298, 325, 326, 327, 328, 329, 330, 331, and 332, wherein numbering is according to the EU index. In another embodiment, modification(s) are at positions selected from the group consisting of 234, 235, 236, 237, 266, 267, 268, 327, 328, according to the EU index. In another embodiment, modification(s) are at positions selected from the group consisting of 235, 236, 266, 267, 268, 328, according to the EU index. In another embodiment, modification(s) are at positions selected from the group consisting of 235, 236, 239, 266, 267, 268, and 328, according to the EU index. In another embodiment, modification(s) are at positions selected from the group consisting of 234, 235, 236, 237, 266, 267, 268, 327, 328, according to the EU index In one embodiment, said modification(s) is at least one substitution (e.g., one or more substitution(s), two or more substitution(s), etc.) selected from the group consisting of 234F, 234G, 234I, 234K, 234N, 234P, 234Q, 234S, 234V, 234W, 234Y, 234D, 234E, 235A, 235E, 235H, 235I, 235N, 235P, 235Q, 235R, 235S, 235W, 235Y, 235D, 235F, 235T, 236D, 236F, 236H, 236I, 236K, 236L, 236M, 236P, 236Q, 236R, 236S, 236T, 236V, 236W, 236Y, 236A, 236E, 236N, 237A, 237E, 237H, 237K, 237L, 237P, 237Q, 237S, 237V, 237Y, 237D, 237N, 239D, 239E, 239N, 239Q, 265E, 266D, 266I, 266M, 267A, 267D, 267E, 267G, 268D, 268E, 268N, 268Q, 298D, 298E, 298L, 298M, 298Q, 325L, 326A, 326E, 326W, 326D, 327D, 327G, 327L, 327N, 327Q, 327E, 328E, 328F, 328Y, 328H, 328I, 328Q, 328W, 329E, 330D, 330H, 330K, 330S, 331S, and 332E, wherein numbering is according to an EU index. In one embodiment, said modification(s) is at least one substitution (e.g., one or more substitution(s), two or more substitution(s), etc.) selected from the group consisting of 234N, 234F, 234D, 234E, 234W, 235Q, 235R, 235W, 235Y, 235D, 235F, 235T, 236D, 236H, 236I, 236L, 236S, 236Y, 236E, 236N, 237H, 237L, 237D, 237N, 239D, 239N, 239E, 266I, 266M, 267A, 267D, 267E, 267G, 268D, 268E, 268N, 268Q, 298E, 298L, 298M, 298Q, 325L, 326A, 326E, 326W, 326D, 327D, 327L, 327E, 328E, 328F, 328Y, 328H, 328I, 328Q, 328W, 330D, 330H, 330K, and 332E, wherein numbering is according to an EU index. In one embodiment, said modification(s) is at least one substitution (e.g., one or more substitution(s), two or more substitution(s), etc.) selected from the group consisting of 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E, wherein numbering is according to an EU index. In one embodiment, said modification(s) is at least one substitution (e.g., one or more substitution(s), two or more substitution(s), etc.) selected from the group consisting of 234E, 235Y, 235R, 236D, 236N, 237N, 266M, 267E, 268E, 268D, 327D, 327E, 328F, 328Y, 328W, wherein numbering is according to an EU index. In one embodiment, said modification(s) is at least one substitution (e.g., one or more substitution(s), two or more substitution(s), etc.) selected from the group consisting of 235Y, 236D, 239D, 266M, 267E, 268D, 268E, 328F, 328W, and 328Y, wherein numbering is according to an EU index. In one embodiment, said modification(s) is at least one substitution (e.g., one or more substitution(s), two or more substitution(s), etc.) selected from the group consisting of 235Y, 236D, 266M, 267E, 268E, 268D, 328F, 328Y, and 328W, wherein numbering is according to an EU index.

In one embodiment, said modification(s) result in at least one of the following combinations of substitutions: 235Y/267E, 236D/267E, 239D/268D, 239D/267E, 239D/332E, 267E/268D, 267E/268E, and 267E/328F, wherein numbering is according to an EU index.

In one embodiment, the modifications disclosed herein reduce affinity to at least one receptor relative to the parent immunoglobulin, wherein said receptor is selected from the group consisting of FcγRI, FcγRIIa, and FcγRIIIa. In this embodiment, immunoglobulin variants disclosed herein may mediate reduced ADCC or ADCP relative to the parent immunoglobulin. In an alternate embodiment, the modifications disclosed herein increase affinity to at least one receptor relative to the parent immunoglobulin, wherein said receptor is selected from the group consisting of FcγRI, FcγRIIa, and FcγRIIIa. In this embodiment, immunoglobulin variants disclosed herein may mediate increased ADCC or ADCP relative to the parent immunoglobulin.

Also disclosed herein are methods for engineering the novel coengagement molecules, including immunoglobulin compositions.

Also disclosed herein are isolated nucleic acids encoding the coengagement molecules, including immunoglobulins described herein. Also disclosed herein are vectors comprising the nucleic acids, optionally, operably linked to control sequences. Also disclosed herein are host cells containing the vectors, and methods for producing and optionally recovering the coengagement molecules.

Also disclosed herein are coengagement molecules that comprise the immunoglobulins disclosed herein. The coengagement molecules may find use in a therapeutic product. In one embodiment, the coengagement molecules disclosed herein may be antibodies.

Also disclosed are compositions comprising coengagement molecules described herein, and a physiologically or pharmaceutically acceptable carrier or diluent.

Also disclosed herein are methods of inhibiting IgE+ FcγRIIb+ cells. The methods of inhibiting cells described herein comprise contacting an IgE+ FcγRIIb+ cell with a coengagement molecule, wherein said coengagement molecule binds FcγRIIb with a Kd of less than about 100 nM. In most preferred embodiments, said coengagement molecule coengages IgE and FcγRIIb on the cell's surface. In preferred embodiments, the inhibition methods comprise contacting an IgE+ FcγRIIb+ cell with an antibody, wherein said antibody binds IgE via its Fv region, and wherein said antibody comprises an Fc region, wherein said Fc region binds FcγRIIb with Kd of 100 nM or less. In other embodiments, said Fc region binds FcγRIIa and/or FcγRIIIa with affinity that is greater relative to native IgG1. In other embodiments, the methods comprise contacting IgE+ FcγRIIb+ cells with a coengagement molecule, wherein said coengagement molecule is a bispecific antibody comprising a first Fv region and a second Fv region, wherein said first Fv region binds IgE, and said second Fv region binds FcγRIIb with a Kd of less than about 100 nM. In alternate embodiments, the methods comprise contacting IgE+ FcγRIIb+ cells with a coengagement molecule, wherein said coengagement molecule is an Fc fusion comprising an Fc region, wherein said Fc region binds FcγRIIb with a Kd of less than about 100 nM.

Other preferred methods include a method of reducing IgE secretion. The method includes contacting an IgE+ FcγRIIb+ cell with a coengagement molecule, wherein said coengagement molecule binds IgE and FcγRIIb with a Kd of less than about 100 nM.

Also included is a method of inhibiting maturation of B-cells. This method includes contacting an IgE+ FcγRIIb+ cell with a coengagement molecule, wherein said coengagement molecule binds IgE and FcγRIIb with a Kd of less than about 100 nM.

Also described are therapeutic and diagnostic uses for the coengagement molecules disclosed herein. In a most preferred embodiment, the coengagement molecules disclosed herein are used to treat one or more IgE-mediated disorders, e.g., autoimmune diseases, inflammatory diseases, etc. that are mediated by immunoglobulin IgE. In particular embodiments, allergic and atopic disorders that may be treated by the compositions disclosed herein include but are not limited to allergic and atopic asthma, atopic dermatitis and eczema, allergic rhinitis, allergic conjunctivitis and rhinoconjunctivitis, allergic encephalomyelitis, allergic rhinitis, allergic vasculitis, anaphylactic shock, and allergies to any variety of environmental or food allergies. The treatment methods disclosed herein comprise administration to a patient in need of such administration a therapeutic amount of a coengagement molecule that coengages IgE and FcγRIIb on a cell's surface.

BRIEF DESCRIPTION OF THE DRAWINGS

FIG. 4. Affinities of Fc variant antibodies for human FcγRs as determined by Biacore surface plasmon resonance. The table provides equilibrium $K_D$'s for binding of variant and WT IgG1 antibodies to human FcγRI, H131 FcγRIIa FcγRIIb, and V158 FcγRIIIa, and the fold binding for each relative to native (WT) IgG1. n.d.=not detectable.

FIG. 5. Amino acid sequences of the heavy (VH) and light (VL) chain variable regions and CDRs of anti-IgE antibodies. CDR boundaries were defined as described previously based on a structural alignment of antibody variable regions (Lazar et al., 2007, Mol Immunol 44:1986-1998) (SEQ ID NOs. 1-32).

FIG. 6. Amino acid sequences of the heavy and light chain WT and variant constant regions (SEQ ID NOs. 33-36).

FIG. 7. Amino acid sequences of anti-IgE full length antibodies that may be used to target IgE+ B cells (SEQ ID NOs. 37-42).

DETAILED DESCRIPTION OF EXEMPLARY EMBODIMENTS

Figure 1:
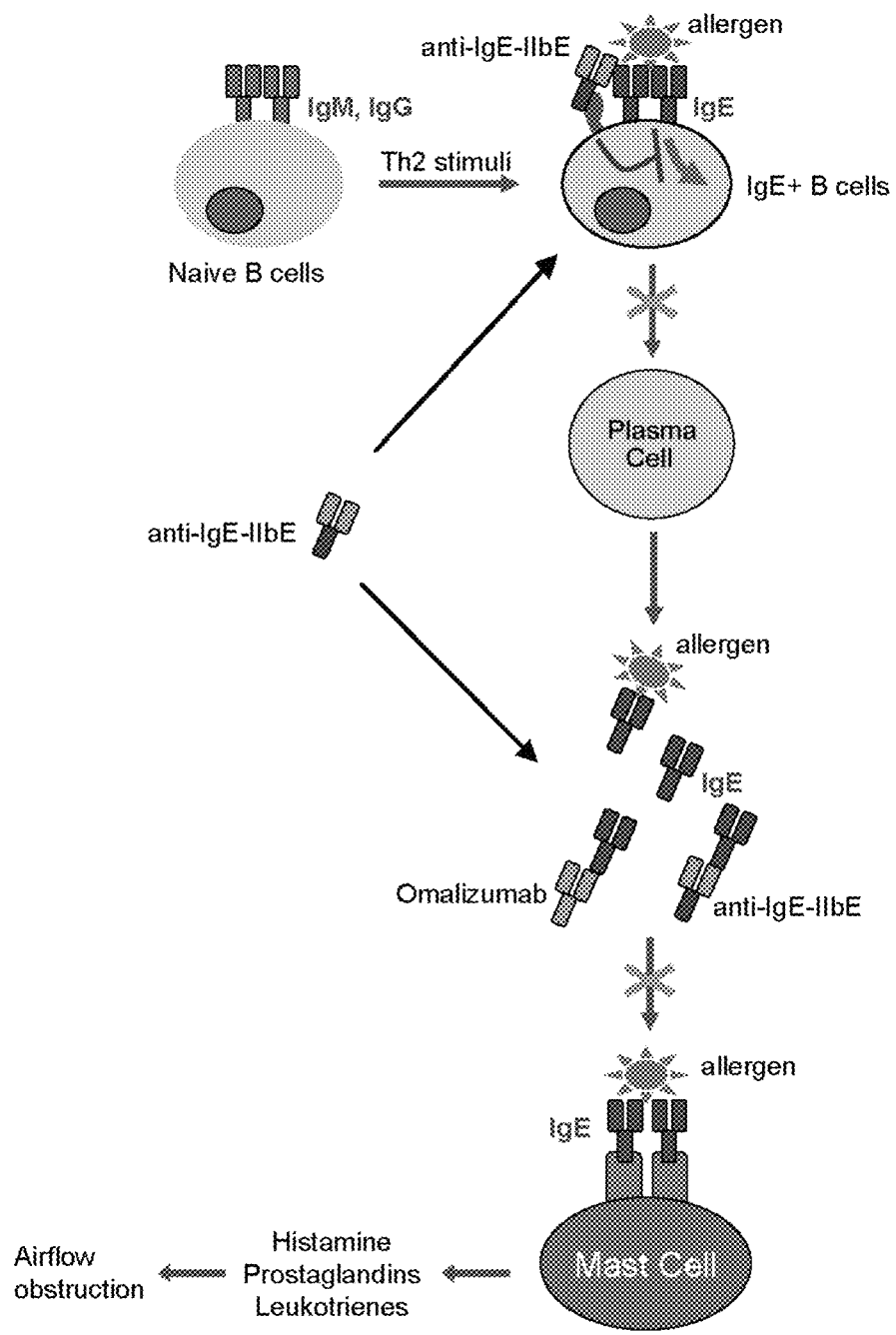
FIG. 1. Illustration of the novel mechanistic approach for inhibiting IgE+ FcγRIIb+ B cells. Under appropriate stimuli, naive B cells can differentiate into IgE+ B cells. Engagement of antigen with the IgE B cell receptor activates these cells, which can then differentiate into plasma cells that release circulating IgE. Binding of circulating IgE binds to FcεR's, for example on mast cells, basophils, and eosinophils, activates these cells. Release of histamine, prostaglandins, and other chemical mediators ultimately results in the clinical symptoms of allergy and asthma. Omalizumab, having a native IgG1 Fc region, is capable of blocking binding of IgE to FcεR. Anti-IgE antibodies with high affinity for FcγRIIb, referred to as Anti-IgE-IIbE in the figure, are capable of not only blocking binding of IgE to FcεR, but also of inhibiting activation of IgE+ B cells by mIgE FcγRIIb coengagement.

Described herein are coengagement molecules that mimic the inhibitory effects of coengagement of membrane-anchored IgE with FcγRIIb on B cells. For example, described herein are variant anti-IgE antibodies engineered such that the Fc domain binds to FcγRIIb with up to ~430-fold greater affinity. Relative to native IgG1, the FcγRIIb binding-enhanced (IIbE) variants strongly inhibit BCR-induced calcium mobilization and viability in primary human IgE+ B cells. The use of a single molecule, such as an antibody to suppress B cell functions by coengagement of cognate IgE BCR and FcγRIIb may represent a novel approach in the treatment of IgE-mediated diseases. Nonlimiting examples of IgE-mediated diseases include allergic responses and asthma and are described in more detail below.

Coengagement molecules according to the disclosure may take on a variety of configurations as outlined in more detail below. In one embodiment the coengagement molecule includes an immunoglobulin that binds IgE and FcγRIIb with high affinity. In this embodiment the immunoglobulin preferably coengages membrane-anchored IgE and FcγRIIb on a cell's surface and binds with a Kd of less than about 100 nM. In another embodiment, the coengagement molecule is a bispecific molecule having a first target specific region and a second target specific region, wherein the first target specific region binds IgE and the second target specific region binds FcγRIIb with a Kd of less than about 100 nM, although in some embodiments it may bind FcγRIIb with a Kd of less than about 10 nM or a Kd of less than about 1 nM and in some embodiments may bind with a Kd less than 100 pM. In a preferred embodiment the coengagement molecule is a bispecific antibody and the first and second target specific regions are Fv regions, wherein the first Fv region binds IgE, and the second Fv region binds FcγRIIb with a Kd of less than about 100 nM. In another embodiment, coengagement molecule is an Fc fusion comprising an Fc region, wherein said Fc region binds FcγRIIb with a Kd of less than about 100 nM. In this embodiment, the Fc fusion partner of the immunoglobulin binds IgE.

Described herein are several definitions. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution S267E refers to a variant polypeptide, in this case a constant heavy chain variant, in which the serine at position 267 is replaced with glutamic acid. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

By "amino acid" and "amino acid identity" as used herein is meant one of the 20 naturally occurring amino acids or any non-natural analogues that may be present at a specific, defined position.

By "CD32b+ cell" or "FcγRIIb+ cell" as used herein is meant any cell or cell type that expresses CD32b (FcγRIIb). CD32b+ cells include but are not limited to B cells, plasma cells, dendritic cells, macrophages, neutrophils, mast cells, basophils, or eosinophils.

By "IgE+ cell" as used herein is meant any cell or cell type that expresses IgE. In preferred embodiments of the invention, IgE+ cells express membrane-anchored IgE (mIgE). IgE+ cells include but are not limited to B cells and plasma cells.

By "CDC" or "complement dependent cytotoxicity" as used herein is meant the reaction wherein one or more complement protein components recognize bound antibody on a target cell and subsequently cause lysis of the target cell.

By "coengagement molecule" or grammatical equivalents is meant a bifunctional molecule capable of binding both IgE and FcγRIIb wherein the Kd for binding of the molecule to FcγRIIb is less than about 100 nM on a cell surface resulting in simultaneous binding of both IgE and FcγRIIb.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of CK or wherein numbering is according to the EU index. By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC.

By "effector cell" as used herein is meant a cell of the immune system that expresses one or more Fc and/or complement receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys.

By "Fab" or "Fab region" as used herein is meant the polypeptides that comprise the $V_H$, CH1, $V_H$, and $C_L$ immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below.

By "Fc polypeptide" as used herein is meant a polypeptide that comprises all or part of an Fc region. Fc polypeptides include antibodies, Fc fusions, isolated Fcs, and Fc fragments. Immunoglobulins may be Fc polypeptides.

By "Fc fusion" as used herein is meant a protein wherein one or more polypeptides is operably linked to Fc. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both hereby entirely incorporated by reference). An Fc fusion combines the Fc region of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, e.g., an extracellular receptor that is implicated in disease.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, incorporated entirely by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "Fc ligand" or "Fc receptor" as used herein is meant a molecule, e.g., a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136). Fc ligands may include undiscovered molecules that bind Fc.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "immunoglobulin" herein is meant a protein comprising one or more polypeptides substantially encoded by immunoglobulin genes. Immunoglobulins include but are not limited to antibodies (including bispecific antibodies) and Fc fusions. Immunoglobulins may have a number of structural forms, including but not limited to full length antibodies, antibody fragments, and individual immunoglobulin domains.

By "immunoglobulin (Ig) domain" as used herein is meant a region of an immunoglobulin that exists as a distinct structural entity as ascertained by one skilled in the art of protein structure. Ig domains typically have a characteristic β-sandwich folding topology. The known Ig domains in the IgG isotype of antibodies are VH Cγ1, Cγ2, Cγ3, VL, and CL.

By "IgG" or "IgG immunoglobulin" or "immunoglobulin G" as used herein is meant a polypeptide belonging to the class of antibodies that are substantially encoded by a recognized immunoglobulin gamma gene. In humans this class comprises the subclasses or isotypes IgG1, IgG2, IgG3, and IgG4.

By "IgE" or "IgE immunoglobulin" or "immunoglobulin E" as used herein is meant a polypeptide belonging to the class of antibodies that are substantially encoded by a recognized immunoglobulin epsilon gene. IgE may be membrane-anchored (mIgE), or non-membrane-anchored, also referred to herein as circulating IgE.

By "inhibition" of cells or grammatical equivalents is meant preventing or reducing the activation, proliferation, maturation or differentiation of targeted cells.

By "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE.

By "modification" herein is meant an alteration in the physical, chemical, or sequence properties of a protein, polypeptide, antibody, or immunoglobulin. Modifications described herein include amino acid modifications and glycoform modifications.

By "glycoform modification" or "modified glycoform" or "engineered glycoform" as used herein is meant a carbohydrate composition that is covalently attached to a protein, for example an antibody, wherein said carbohydrate composition differs chemically from that of a parent protein. Modified glycoform typically refers to the different carbohydrate or oligosaccharide; thus for example an Fc variant may comprise a modified glycoform. Alternatively, modified glycoform may refer to the Fc variant that comprises the different carbohydrate or oligosaccharide.

By "parent polypeptide", "parent protein", "parent immunogloblin", "precursor polypeptide", "precursor protein", or "precursor immunoglobulin" as used herein is meant an unmodified polypeptide, protein, or immunoglobulin that is subsequently modified to generate a variant, e.g., any polypeptide, protein or immunoglobulin which serves as a template and/or basis for at least one amino acid modification described herein. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant Fc polypeptide, and by "parent antibody" as used herein is meant an antibody that is modified to generate a variant antibody (e.g., a parent antibody may include, but is not limited to, a protein comprising the constant region of a naturally occurring Ig).

By "position" as used herein is meant a location in the sequence of a protein. Positions may be numbered sequentially, or according to an established format, for example the EU index as described in Kabat. For example, position 297 is a position in the human antibody IgG1.

By "polypeptide" or "protein" as used herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound by the variable region of a given antibody, or the fusion partner of an Fc fusion. A target antigen may be a protein, carbohydrate, lipid, or other chemical compound. An antibody or Fc fusion is said to be "specific" for a given target antigen based on having affinity for the target antigen.

By "target cell" as used herein is meant a cell that expresses a target antigen.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "variant polypeptide", "polypeptide variant", or "variant" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. In some embodiments, variant polypeptides disclosed herein (e.g., variant immunoglobulins) may have at least one amino acid modification compared to the parent polypeptide, e.g. from about one to about ten amino acid modifications, from about one to about five amino acid modifications, etc. compared to the parent. The variant polypeptide sequence herein may possess at least about 80% homology with a parent polypeptide sequence, e.g., at least about 90% homology, 95% homology, etc. Accordingly, by "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it. By "Fc polypeptide variant" or "variant Fc polypeptide" as used herein is meant an Fc polypeptide that differs from a parent Fc polypeptide by virtue of at least one amino acid modification. By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

By "wild type" or "WT" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

Coengagement Molecules

As described herein coengagement molecules are bifunctional molecules capable of binding to FcγRIIb and IgE on the surface of a cell. These molecules may take on a variety of configurations as outlined in more detail herein. Preferably the coengagement molecules are proteinaceous, although this is not necessarily required. In some embodiments the coengagement molecule can be a bifunctional molecule in which specificity for FcγRIIb and/or IgE is conferred by a small molecule, nucleic acid and/or polypeptide, for example. Preferably the coengagement molecule binds FcγRIIb with a Kd of less than about 100 nM. In a preferred embodiment the coengagement molecule includes an immunoglobulin that binds IgE and FcγRIIb with high affinity. In this embodiment the immunoglobulin preferably coengages membrane-anchored IgE and FcγRIIb on a cell's surface. In another embodiment, the coengagement molecule is a bispecific molecule having a first target specific region and a second target specific region, wherein the first target specific region binds IgE and the second target specific region binds FcγRIIb with a Kd of less than about 100 nM. In a preferred embodiment the coengagement molecule is a bispecific antibody and the first and second target specific regions are Fv regions, wherein the first Fv region binds IgE, and the second Fv region binds FcγRIIb with a Kd of less than about 100 nM. In another embodiment, the coengagement molecule is an Fc fusion comprising an Fc region, wherein said Fc region binds FcγRIIb with a Kd of less than about 100 nM. In this embodiment, the Fc fusion partner of the immunoglobulin binds IgE.

In one embodiment the coengagement molecule is a bifunctional molecule in which a first region binds IgE and a second region binds FcγRIIb with a Kd of less than about 100 nM. Virtually any protein, small molecule or nucleic acid, e.g. aptamers, may be linked to generate the bifunctional binding molecule and may include linkers as outlined herein. In a preferred embodiment protein fusion partners may include, but are not limited to, the variable region of an antibody, the target-binding region of a receptor, an adhesion molecule, a ligand, an enzyme, a cytokine, a chemokine, or some other protein or protein domain. Small molecule fusion partners may include any agent that directs the coengagement molecule to a target antigen, such as IgE. For example, in preferred embodiments, the coengagement molecule may comprise FcεRI or FcεRII/CD23 as a fusion partner. In preferred embodiments immunoglobulins find use as coengagement molecules.

Immunoglobulins

As described herein, an immunoglobulin is a preferred component of a coengagement molecule and may be an antibody, an Fc fusion, an isolated Fc, an Fc fragment, or an Fc polypeptide. In one embodiment, an immunoglobulin is an antibody. As outlined in more detail below the immunoglobulin finds use as a bifunctional molecule in which the Fv region binds IgE and the Fc region binds FcγRIIb with a Kd of less than about 100 nM. In addition, an antibody finds use in Fc fusions or bifunctional antibodies as outlined below.

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Each of the light and heavy chains are made up of two distinct regions, referred to as the variable and constant regions. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively. The constant regions show less sequence diversity, and are responsible for binding a number of natural proteins to elicit important biochemical events. The distinguishing features between these antibody classes are their constant regions, although subtler differences may exist in the variable region.

The variable region of an antibody contains the antigen binding determinants of the molecule, and thus determines the specificity of an antibody for its target antigen. The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, hereby entirely incorporated by reference, and the conserved features of antibodies are disclosed, for example, in Maynard et al., 2000, Annu Rev Biomed Eng 2:339-376, hereby entirely incorporated by reference.

The carboxy-terminal portion of each chain defines a constant region primarily responsible for effector function. In the IgG subclass of immunoglobulins, there are several immunoglobulin domains in the heavy chain. By "immunoglobulin (Ig) domain" herein is meant a region of an immunoglobulin having a distinct tertiary structure. Of interest in embodiments described herein are the heavy chain domains, including, the constant heavy (CH) domains and the hinge region. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another important region of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230 to 236.

Of interest in embodiments described herein are the Fc regions. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the lower hinge region between Cgamma1 (Cγ1) and Cgamma2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

The Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290, both hereby entirely incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, hereby entirely incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γγ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, both hereby entirely incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65, hereby entirely incorporated by reference). The FcγRs bind the IgG Fc region with different affinities. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge. This interaction is well characterized structurally (Sondermann et al., 2001, J Mol Biol 309:737-749, hereby entirely incorporated by reference), and several structures of the human Fc bound to the extracellular domain of human FcγRIIIb have been solved (pdb accession code 1E4K) (Sondermann et al., 2000, Nature 406:267-273, hereby entirely incorporated by reference) (pdb accession codes 1IIS and 1IIX) (Radaev et al., 2001, J Biol Chem 276:16469-16477, hereby entirely incorporated by reference).

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-

766, both hereby entirely incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins (Umana et al., 1999, Nat Biotechnol 17:176-180; Davies et al., 2001, Biotechnol Bioeng 74:288-294; Mimura et al., 2001, J Biol Chem 276:45539-45547; Radaev et al., 2001, J Biol Chem 276:16478-16483; Shields et al., 2001, J Biol Chem 276:6591-6604; Shields et al., 2002, J Biol Chem 277:26733-26740; Simmons et al., 2002, J Immunol Methods 263:133-147, all hereby entirely incorporated by reference).

Immunoglobulins of embodiments described herein may also be an antibody-like protein referred to as an Fc fusion (Chamow et al., 1996, *Trends Biotechnol* 14:52-60; Ashkenazi et al., 1997, *Curr Opin Immunol* 9:195-200, both incorporated entirely by reference). "Fc fusion" is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion is a protein wherein one or more polypeptides, herein referred to as a "fusion partner", is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present disclosure extends also to Fc fusions.

Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any agent that directs the Fc fusion to a target antigen. Such target antigen may be any molecule, e.g., an extracellular receptor, that is implicated in disease. Fc fusions of embodiments described herein preferably have specificity for IgE. For example, in preferred embodiments, Fc fusions of the invention may comprise FcεRI or FcεRII/CD23 as a fusion partner. Fc fusions of the invention preferably comprise one or more variants in the Fc region that enhance affinity for FcγRIIb.

Fusion partners may be linked to any region of an Fc region, including at the N- or C-termini, or at some residue in-between the termini. In one embodiment, a fusion partner is linked at the N- or C-terminus of the Fc region. A variety of linkers may find use in some embodiments described herein to covalently link Fc regions to a fusion partner. By "linker", "linker sequence", "spacer", "tethering sequence" or grammatical equivalents thereof, herein is meant a molecule or group of molecules (such as a monomer or polymer) that connects two molecules and often serves to place the two molecules in a configuration. Linkers are known in the art; for example, homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length. In one embodiment, h linkers of 1 to 20 amino acids in length may be used. Useful linkers include glycine-serine polymers (including, for example, (GS)n, (GSGGS)n (set forth as SEQ ID NO:43), (GGGGS)n (set forth as SEQ ID NO:44), and (GGGS)n (set forth as SEQ ID NO:45), where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link an Fc regions to a fusion partner.

Also contemplated as fusion partners are Fc polypeptides. Thus an immunoglobulin as described herein may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab's and Fc's may be linked by thioether bonds originating at cysteine residues in the hinges, generating molecules such as FabFc$_2$. Fc regions may be linked using disulfide engineering and/or chemical cross-linking. In one embodiment, Fc regions may be linked genetically. In one embodiment, Fc regions in an immunoglobulin are linked genetically to generated tandemly linked Fc regions as described in U.S. Ser. No. 11/022,289, filed Dec. 21, 2004, entitled "Fc polypeptides with novel Fc ligand binding sites," incorporated entirely by reference. Tandemly linked Fc polypeptides may comprise two or more Fc regions, e.g., one to three Fc regions, two Fc regions. It may be advantageous to explore a number of engineering constructs in order to obtain homo- or hetero-tandemly linked Fc regions with the most favorable structural and functional properties. Tandemly linked Fc regions may be homo-tandemly linked Fc regions, that is an Fc region of one isotype is fused genetically to another Fc region of the same isotype. It is anticipated that because there are multiple FcγR, Gig, and/or FcRn binding sites on tandemly linked Fc polypeptides, effector functions and/or pharmacokinetics may be enhanced. In an alternate embodiment, Fc regions from different isotypes may be tandemly linked, referred to as hetero-tandemly linked Fc regions. For example, because of the capacity to target FcγR and FcαRI receptors, an immunoglobulin that binds both FcγRs and FcαRI may provide a significant clinical improvement.

The immunoglobulins of embodiments disclosed herein may be substantially encoded by immunoglobulin genes belonging to any of the antibody classes. In certain embodiments, the immunoglobulins disclosed herein find use in antibodies or Fc fusions that comprise sequences belonging to the IgG class of antibodies, including IgG1, IgG2, IgG3, or IgG4. FIG. 1 provides an alignment of these human IgG sequences. In alternate embodiments, immunoglobulins disclosed herein find use in antibodies or Fc fusions that comprise sequences belonging to the IgA (including subclasses IgA1 and IgA2), IgD, IgE, IgG, or IgM classes of antibodies. The immunoglobulins disclosed herein may comprise more than one protein chain, e.g., may be an antibody or Fc fusion that is a monomer or an oligomer, including a homo- or hetero-oligomer.

Immunoglobulins disclosed herein may be substantially encoded by genes from any organism, e.g., mammals (including, but not limited to humans, rodents (including but not limited to mice and rats), lagomorpha (including but not limited to rabbits and hares), camelidae (including but not limited to camels, llamas, and dromedaries), and non-human primates, including but not limited to Prosimians, Platyrrhini (New World monkeys), Cercopithecoidea (Old World monkeys), and Hominoidea including the Gibbons and Lesser and Great Apes. In a certain embodiments, the immunoglobulins disclosed herein may be substantially human.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both hereby entirely incorporated by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. The immunoglobulins disclosed herein may be substantially encoded by any allotype, isoallotype, or haplotype of any immunoglobulin gene.

The immunoglobulins disclosed herein may compose an Fc polypeptide, including but not limited to antibodies, isolated Fcs, Fc fragments, and Fc fusions. In one embodiment, an immunoglobulin disclosed herein is a full length antibody, constituting the natural biological form of an antibody, including variable and constant regions. For the IgG isotype full length antibody is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In another embodiment, immunoglobulins disclosed herein are isolated Fc regions or Fc fragments.

Immunoglobulins disclosed herein may be a variety of structures, including, but not limited antibody fragments, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

Nonhuman, Chimeric, Humanized, and Fully Human Antibodies

The variable region of an antibody, as is well known in the art, can compose sequences from a variety of species. In some embodiments, the antibody variable region can be from a nonhuman source, including but not limited to mice, rats, rabbits, camels, llamas, and monkeys. In some embodiments, the scaffold components can be a mixture from different species. As such, an antibody disclosed herein may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,693,762, incorporated entirely by reference. The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084. Structure-based methods may be employed for humanization and affinity maturation, for example as described in U.S. Ser. No. 10/153,159 and related applications, all incorporated entirely by reference. In certain variations, the immunogenicity of the antibody is reduced using a method described in Lazar et al., 2007, Mol Immunol 44:1986-1998 and U.S. Ser. No. 11/004,590, entitled "Methods of Generating Variant Proteins with Increased Host String Content and Compositions Thereof", filed on Dec. 3, 2004, incorporated entirely by reference.

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108). In one embodiment human equivalent antibodies may generated computationally as outlined in PCT/US09/41144, which is incorporated herein by reference.

Anti-IgE Antibodies

The immunoglobulins described herein bind IgE. The anti-IgE antibodies of the invention may comprise any variable region, known or not yet known, that has specificity for IgE. Known anti-IgE antibodies include but are not limited to murine antibodies MaE11, MaE13, and MaE15, humanized and/or engineered versions of these antibodies including E25, E26, and E27, particularly E25, also known as rhuMab-E25, also known as Omalizumab, such as those described in U.S. Pat. No. 6,761,889, U.S. Pat. No. 6,329,509, US20080003218A1, and Presta, L G et al., 1993, J Immunol 151:2623-2632, all herein expressly incorporated by reference. A preferred engineered version of MaE11 is H1 L1 MaE11, described in the Examples herein. Other anti-IgE that may be useful for the invention include murine antibody TES-C21, chimeric TES-C21, also known as CGP51901 (Come, J et al., 1997, J Clin Invest 99:879-887; Racine-Poon, A et al., 1997, Clin Pharmcol Ther 62:675-690), and humanized and/or engineered versions of this antibody including but not limited to CGP56901, also known as TNX-901, such as those antibodies described in Kolbinger, F et al., 1993, Protein Eng 6:971-980. Other anti-IgE antibodies that may find use for the invention are described in U.S. Pat. No. 6,066,718, U.S. Pat. No. 6,072,035, PCT/US04/02894, U.S. Pat. No. 5,342,924, U.S. Pat. No. 5,091,313, U.S. Pat. No. 5,449,760, U.S. Pat. No. 5,543,144, U.S. Pat. No. 5,342,924, and U.S. Pat. No. 5,614,611, all of which are incorporated herein by reference. Other useful anti-IgE antibodies include the murine antibody BSW17. Amino acid sequences of the variable region VH and VL domains and CDRs of some of these antibodies are provided in FIG. 5.

Fc Variants and Fc Receptor Binding Properties

Immunoglobulins disclosed herein may comprise an Fc variant. An Fc variant comprises one or more amino acid modifications relative to a parent Fc polypeptide, wherein the amino acid modification(s) provide one or more optimized properties. An Fc variant disclosed herein differs in amino acid sequence from its parent by virtue of at least one amino acid modification. Thus Fc variants disclosed herein have at least one amino acid modification compared to the parent. Alternatively, the Fc variants disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein include amino acid modifications, including insertions, deletions, and substitutions. Modifications disclosed herein also include glycoform modifications. Modifications may be made genetically using molecular biology, or may be made enzymatically or chemically.

Fc variants disclosed herein are defined according to the amino acid modifications that compose them. Thus, for example, S267E is an Fc variant with the substitution S267E relative to the parent Fc polypeptide. Likewise, S267E/L328F defines an Fc variant with the substitutions S267E and L328F relative to the parent Fc polypeptide. The identity of the WT amino acid may be unspecified, in which case the aforementioned variant is referred to as 267E/328F. It is noted that the order in which substitutions are provided is arbitrary, that is to say that, for example, 267E/328F is the same Fc variant as 328F/267E, and so on. Unless otherwise noted, positions discussed herein are numbered according to the EU index or EU numbering scheme (Kabat et al., 1991, Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgGD, IgGM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

The Fc variants disclosed herein may be optimized for a variety of Fc receptor binding properties. An Fc variant that is engineered or predicted to display one or more optimized properties is herein referred to as an "optimized Fc variant". Properties that may be optimized include but are not limited to enhanced or reduced affinity for an FcγR. In one embodiment, the Fc variants disclosed herein are optimized to possess enhanced affinity for an inhibitory receptor FcγRIIb. In other embodiments, immunoglobulins disclosed herein provide enhanced affinity for FcγRIIb, yet reduced affinity for one or more activating FcγRs, including for example FcγRI, FcγRIIa, FcγRIIIa, and/or FcγRIIIb. The FcγR receptors may be expressed on cells from any organism, including but not limited to human, cynomolgus monkeys, and mice. The Fc variants disclosed herein may be optimized to possess enhanced affinity for human FcγRIIb.

By "greater affinity" or "improved affinity" or "enhanced affinity" or "better affinity" than a parent Fc polypeptide, as used herein is meant that an Fc variant binds to an Fc receptor with a significantly higher equilibrium constant of association ($K_A$ or Ka) or lower equilibrium constant of dissociation ($K_D$ or Kd) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore, by one skilled in the art. Accordingly, by "reduced affinity" as compared to a parent Fc polypeptide as used herein is meant that an Fc variant binds an Fc receptor with significantly lower $K_A$ or higher $K_D$ than the parent Fc polypeptide. Greater or reduced affinity can also be defined relative to an absolute level of affinity. For example, according to the data herein, WT (native) IgG1 binds FcγRIIb with an affinity of about 2 μM, or about 2000 nM. Furthermore, some Fc variants described herein bind FcγRIIb with an affinity about 10-fold greater to WT IgG1. As disclosed herein, greater or enhanced affinity means having a $K_D$ lower than about 100 nM, for example between about 10 nM-about 100 nM, between about 1-about 100 nM, or less than about 1 nM.

Anti-IgE antibodies of the invention preferably have high affinity for FcγRIIb. By high affinity herein is meant that the affinity of the interaction between the antibody and FcγRIIb is stronger than 100 nM. That is to say that the equilibrium dissociation constant Kd for binding of the antibody to FcγRIIb is lower than 100 nM.

In one embodiment, the Fc variants provide selectively enhanced affinity to FcγRIIb relative to one or more activating receptors. Selectively enhanced affinity means either that the Fc variant has improved affinity for FcγRIIb relative to the activating receptor(s) as compared to the parent Fc polypeptide but has reduced affinity for the activating receptor(s) as compared to the parent Fc polypeptide, or it means that the Fc variant has improved affinity for both FcγRIIb and activating receptor(s) as compared to the parent Fc polypeptide, however the improvement in affinity is greater for FcγRIIb than it is for the activating receptor(s). In alternate embodiments, the Fc variants reduce or ablate binding to one or more activating FcγRs, reduce or ablate binding to one or more complement proteins, reduce or ablate one or more FcγR-mediated effector functions, and/or reduce or ablate one or more complement-mediated effector functions.

The presence of different polymorphic forms of FcγRs provides yet another parameter that impacts the therapeutic utility of the Fc variants disclosed herein. Whereas the specificity and selectivity of a given Fc variant for the different classes of FcγRs significantly affects the capacity of an Fc variant to target a given antigen for treatment of a given disease, the specificity or selectivity of an Fc variant for different polymorphic forms of these receptors may in part determine which research or pre-clinical experiments may be appropriate for testing, and ultimately which patient populations may or may not respond to treatment. Thus the specificity or selectivity of Fc variants disclosed herein to Fc receptor polymorphisms, including but not limited to FcγRIIa, FcγRIIIa, and the like, may be used to guide the selection of valid research and pre-clinical experiments, clinical trial design, patient selection, dosing dependence, and/or other aspects concerning clinical trials.

Fc variants disclosed herein may comprise modifications that modulate interaction with Fc receptors other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

An important parameter that determines the most beneficial selectivity of a given Fc variant to treat a given disease is the context of the Fc variant. Thus the Fc receptor selectivity or specificity of a given Fc variant will provide different properties depending on whether it composes an antibody, Fc fusion, or Fc variants with a coupled fusion partner. In one embodiment, an Fc receptor specificity of the Fc variant disclosed herein will determine its therapeutic utility. The utility of a given Fc variant for therapeutic purposes will depend on the epitope or form of the target antigen and the disease or indication being treated. For some targets and indications, greater FcγRIIb affinity and reduced activating FcγR-mediated effector functions may be beneficial. For other target antigens and therapeutic applications, it may be beneficial to increase affinity for FcγRIIb, or increase affinity for both FcγRIIb and activating receptors.

Means for Optimizing Activity of Anti-IgE Antibodies

Described herein are means for altering affinity to one or more FcγRs. In a preferred embodiment, affinity is altered to the inhibitory receptor FcγRIIb, thereby altering the ability of the immunoglobulin to mediate one or more FcγRIIb-mediated inhibitory effector functions. Means of the invention include amino acid modifications (e.g., positional means for optimizing function, substitutional means for optimizing function, etc.) and glycoform modifications (e.g., means for glycoform modifications).

Amino Acid Modifications

Disclosed herein are immunoglobulins comprising amino acid modifications, wherein said modifications alter affinity to one or more FcγRs. Preferably, said amino acid modifications improve affinity to FcγRIIb. However in some embodiments, modifications may improve affinity to one or more activating receptors, for example FcγRI, FcγRIIa, and FcγRIIIa. Modifications for altering binding to FcγRs are described in U.S. Ser. No. 11/124,620, filed May 5, 2005, entitled "Optimized Fc Variants", and U.S. Ser. No. 12/156,183, filed May 30, 2008, entitled "Methods and Compositions for Inhibiting CD32b Expressing Cells", both herein expressly incorporated by reference.

As described herein, positional means for optimizing activity of anti-IgE antibodies include but are not limited to, modification of an amino acid at one or more heavy chain constant region positions (e.g., at positions: 234, 235, 236, 237, 239, 265, 266, 267, 268, 298, 325, 326, 327, 328, 329, 330, 331, and 332) which allow modification of immunoglobulin FcγRIIb binding properties, effector function, and potentially clinical properties of antibodies.

In particular, substitutional means for optimizing activity of anti-IgE antibodies, e.g., by altering affinity to FcγRIIb, include but are not limited to, a substitution of an amino acid at one or more heavy chain constant region positions, e.g., one or more of the amino acid substitutions in the following heavy chain constant region positions: 234, 235, 236, 237, 239, 265, 266, 267, 268, 298, 325, 326, 327, 328, 329, 330, 331, and 332, wherein numbering is according to the EU index. In one embodiment, substitutional means include at least one (e.g., two or more) substitution(s) compared to a parent Fc region, wherein said modification(s) are at positions selected from the group consisting of 234, 235, 236, 237, 239, 266, 267, 268, 325, 326, 327, 328, and 332, according to the EU index. In one embodiment, substitutional means include one or more (e.g., two or more) substitutions(s) at positions selected from the group consisting of 235, 236, 239, 266, 267, 268, and 328, according to the EU index.

In one embodiment, said substitutional means is at least one substitution (e.g., one or more substitution(s), two or more substitution(s), etc.) selected from the group consisting of 234F, 234G, 234I, 234K, 234N, 234P, 234Q, 234S, 234V, 234W, 234Y, 234D, 234E, 235A, 235E, 235H, 235I, 235N, 235P, 235Q, 235R, 235S, 235W, 235Y, 235D, 235F, 235T, 236D, 236F, 236H, 236I, 236K, 236L, 236M, 236P, 236Q, 236R, 236S, 236T, 236V, 236W, 236Y, 236A, 236E, 236N, 237A, 237E, 237H, 237K, 237L, 237P, 237Q, 237S, 237V, 237Y, 237D, 237N, 239D, 239E, 239N, 239Q, 265E, 266D, 266I, 266M, 267A, 267D, 267E, 267G, 268D, 268E, 268N, 268Q, 298D, 298E, 298L, 298M, 298Q, 325L, 326A, 326E, 326W, 326D, 327D, 327G, 327L, 327N, 327Q, 327E, 328E, 328F, 328Y, 328H, 328I, 328Q, 328W, 329E, 330D, 330H, 330K, 330S, 331S, and 332E, wherein numbering is according to an EU index. In one embodiment, said substitutional means is at least one substitution (e.g., one or more substitution(s), two or more substitution(s), etc.) selected from the group consisting of 234N, 234F, 234D, 234E, 234W, 235Q, 235R, 235W, 235Y, 235D, 235F, 235T, 236D, 236H, 236I, 236L, 236S, 236Y, 236E, 236N, 237H, 237L, 237D, 237N, 239D, 239N, 239E, 266I, 266M, 267A, 267D, 267E, 267G, 268D, 268E, 268N, 268Q, 298E, 298L, 298M, 298Q, 325L, 326A, 326E, 326W, 326D, 327D, 327L, 327E, 328E, 328F, 328Y, 328H, 328I, 328Q, 328W, 330D, 330H, 330K, and 332E, wherein numbering is according to an EU index. In one embodiment, said substitutional means is at least one substitution (e.g., one or more substitution(s), two or more substitution(s), etc.) selected from the group consisting of 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E, wherein numbering is according to an EU index. In one embodiment, said substitutional means is at least one substitution (e.g., one or more substitution(s), two or more substitution(s), etc.) selected from the group consisting of 235Y, 236D, 239D, 266M, 267E, 268D, 268E, 328F, 328W, and 328Y, wherein numbering is according to an EU index.

In one embodiment, said substitutional means is at least two substitutions (e.g., a combination of modifications) at positions selected from the group consisting of 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332, wherein numbering is according to an EU index. In one embodiment, said substitutional means is at least two substitutions (e.g., a combination of modifications) at positions selected from the group consisting of 235/267, 236/267, 239/268, 239/267, 267/268, and 267/328, wherein numbering is according to an EU index. In one embodiment, said substitutional means is at least two substitutions (e.g., a combination of substitutions) selected from the group consisting of 234D/267E, 234E/267E, 234F/267E, 234E/328F, 234W/239D, 234W/239E, 234W/267E, 234W/328Y, 235D/267E, 235D/328F, 235F/239D, 235F/267E, 235F/328Y, 235Y/236D, 235Y/239D, 235Y/267D, 235Y/267E, 235Y/268E, 235Y/328F, 236D/239D, 236D/267E, 236D/268E, 236D/328F, 236N/267E, 237D/267E, 237N/267E, 239D/267D, 239D/267E, 239D/268D, 239D/268E, 239D/327D, 239D/328F, 239D/328W, 239D/328Y, 239D/332E, 239E/267E, 266M/267E, 267D/268E, 267E/268D, 267E/268E, 267E/325L, 267E/327D, 267E/327E, 267E/328F, 267E/328I, 267E/328Y, 267E/332E, 268D/327D, 268D/328F, 268D/328W, 268D/328Y, 268D/332E, 268E/328F, 268E/328Y, 327D/328Y, 328F/332E, 328W/332E, and 328Y/332E, wherein numbering is according to an EU index.

In one embodiment, said substitutional means result in at least one of the following substitutions, or combinations of substitutions: 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 235Y/267E, 236D/267E, 236E/267E, 236N/267E, 237D/267E, 237N/267E, 239D/267D, 239D/267E, 266M/267E, 234E/268D, 236D/268D, 239D/268D, 267D/268D, 267D/268E, 267E/268D, 267E/268E, 267E/325L, 267D/327D, 267D/327E, 267E/327D, 267E/327E, 268D/327D, 239D/328Y, 267E/328F, 267E/328H, 267E/328I, 267E/328Q, 267E/328Y, 268D/328Y, 239D/332E, 328Y/332E, 234D/236N/267E, 235Y/236D/267E, 234W/239E/267E, 235Y/239D/267E, 236D/239D/267E, 235Y/267E/268E, 236D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E, wherein numbering is according to an EU index. In one embodiment, said substitutional means result in at least one of the following substitutions, or combinations of substitutions: 266D, 234F/236N, 234F/236D, 236A/237A, 236S/237A, 235D/239D, 234D/267E, 234E/267E, 234F/267E, 235D/267E, 235F/267E, 235S/267E, 235T/267E, 235Y/267D, 236D/267E, 236E/267E, 236N/267E, 237D/267E, 237N/267E, 266M/267E, 234E/268D, 236D/268D, 267D/268D, 267D/268E, 267E/268D, 267E/268E, 267E/325L, 267D/327D, 267D/327E, 267E/327E, 268D/327D, 267E/327E, 268D/327D, 239D/328Y, 267E/328F, 267E/328H, 267E/328I, 267E/328Q, 267E/328Y, 268D/328Y, 234D/236N/267E, 235Y/236D/267E, 234W/239E/267E, 235Y/239D/267E, 236D/239D/267E, 235Y/267E/268E, 236D/267E/268E, 239D/267E/268E, 234W/239D/328Y, 235F/239D/328Y, 234E/267E/328F, 235D/267E/328F, 235Y/267E/328F, 236D/267E/328F, 239D/267A/328Y, 239D/267E/328F, 234W/268D/328Y, 235F/268D/328Y, 239D/268D/328F, 239D/268D/328W, 239D/268D/328Y, 239D/268E/328Y, 267A/268D/328Y, 267E/268E/328F, 239D/326D/328Y, 268D/326D/328Y, 239D/327D/328Y, 268D/327D/328Y, 239D/267E/332E, 234W/328Y/332E, 235F/328Y/332E, 239D/328F/332E, 239D/328Y/332E, 267A/328Y/332E, 268D/328F/332E, 268D/328W/332E, 268D/328Y/332E, 268E/328Y/332E, 326D/328Y/332E, 327D/328Y/332E, 234W/236D/239E/267E, 239D/268D/328F/332E, 239D/268D/328W/332E, and 239D/268D/328Y/332E In one embodiment, said substitutional means result in at least one of the following substitutions, or combinations of substitutions: 235Y/267E, 236D/267E, 239D/268D, 239D/267E, 267E/268D, 267E/268E, and 267E/328F, wherein numbering is according to an EU index.

In some embodiments of the invention, immunoglobulin may comprise means for isotypic modifications, that is, modifications in a parent IgG to the amino acid type in an alternate IgG. For example, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 422I, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, −236G (referring to an insertion of a glycine at position 236), and 327A.

Glycoform Modifications

Many polypeptides, including antibodies, are subjected to a variety of posttranslational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation (Lifely et al., 1995, Glycobiology 5(8): 813-822).

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate (Jefferis et al., 1998, Immunol. Rev. 163:59-76; Wright et al., 1997, Trends Biotech 15:26-32). For human IgG, the core oligosaccharide normally consists of $GlcNAc_2Man_3GlcNAc$, with differing numbers of outer residues.

The carbohydrate moieties of immunoglobulins disclosed herein will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of immunoglobulins disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991).

For the purposes herein, a "mature core carbohydrate structure" refers to a processed core carbohydrate structure attached to an Fc region which generally consists of the following carbohydrate structure $GlcNAc(Fucose)-GlcNAc-Man-(Man-GlcNAc)_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyltransferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

Described herein are Fc variants that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the immunoglobulins disclosed herein are modified to control the level of fucosylated and/or bisecting oligosaccharides that are covalently attached to the Fc region.

A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the IgG has been expressed. Other methods for modifying glycoforms of the immunoglobulins disclosed herein include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass Fc variants with modified glycoforms irrespective of how they are produced.

In one embodiment, immunoglobulins disclosed herein are glycoengineered to alter the level of sialylation. Higher levels of sialylated Fc glycans in immunoglobulin G molecules can adversely impact functionality (Scallon et al., 2007, Mol Immunol. 44(7):1524-34), and differences in levels of Fc sialylation can result in modified anti-inflammatory activity (Kaneko et al., 2006, Science 313:670-673). Because antibodies may acquire anti-inflammatory properties upon sialylation of Fc core polysaccharide, it may be advantageous to glycoengineer the immunoglobulins disclosed herein for greater or reduced Fc sialic acid content.

Engineered glycoform typically refers to the different carbohydrate or oligosaccharide; thus for example an immuoglobulin may comprise an engineered glycoform. Alternatively, engineered glycoform may refer to the immunoglobulin that comprises the different carbohydrate or oligosaccharide. In one embodiment, a composition disclosed herein comprises a glycosylated Fc variant having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated Fc variant having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated Fc variant having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

Other Modifications

Immunoglobulins disclosed herein may comprise one or more modifications that provide optimized properties that are not specifically related to FcγR- or complement-mediated effector functions per se. Said modifications may be amino acid modifications, or may be modifications that are made enzymatically or chemically. Such modification(s) likely provide some improvement in the immunoglobulin, for example an enhancement in its stability, solubility, function, or clinical use. Disclosed herein are a variety of improvements that may be made by coupling the immunoglobulins disclosed herein with additional modifications.

In one embodiment, the variable region of an antibody disclosed herein may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen. Immunoglobulins disclosed herein may comprise one or more modifications that provide reduced or enhanced internalization of an immunoglobulin.

In one embodiment, modifications are made to improve biophysical properties of the immunoglobulins disclosed herein, including but not limited to stability, solubility, and oligomeric state. Modifications can include, for example, substitutions that provide more favorable intramolecular interactions in the immunoglobulin such as to provide greater stability, or substitution of exposed nonpolar amino acids with polar amino acids for higher solubility. Other modifications to the immunoglobulins disclosed herein include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. Additional modifications to the variants disclosed herein include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. Additional modifications include modifications in the hinge and CH3 domains, in which the modifications reduce the propensity to form dimers.

In further embodiments, the immunoglobulins disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and glutamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983), incorporated entirely by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The immunoglobulins disclosed herein may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635):964-7, all incorporated entirely by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the immunoglobulin may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the immunoglobulins. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the immunoglobulins disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein. See for example U.S. Ser. No. 09/903,378, U.S. Ser. No. 10/754,296, U.S. Ser. No. 11/249,692, and references cited therein, all expressly incorporated by reference.

In some embodiments, immunoglobulins disclosed herein may be combined with immunoglobulins that alter FcRn binding. Such variants may provide improved pharmacokinetic properties to the immunoglobulins. Preferred variants that increase binding to FcRn and/or improve pharmacokinetic properties include but are not limited to substitutions at positions 259, 308, 428, and 434, including but not limited to for example 259I, 308F, 428L, 428M, 434S, 434H, 434F, 434Y, and 434M (PCT/US2008/088053, filed Dec. 22, 2008, entitled "Fc Variants with Alterned Binding to FcRn", entirely incorporated by reference). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 311A, 312A, 376A, 378Q, 380A, 382A, 434A (Shields et al, Journal of Biological Chemistry, 2001, 276(9): 6591-6604, entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311 S (DaII Acqua et al. Journal of Immunology, 2002, 169:5171-5180, Dall'Acqua et al., 2006, The Journal of biological chemistry 281:23514-23524, entirely incorporated by reference).

Covalent modifications of antibodies are included within the scope of immunoglobulins disclosed herein, and are generally, but not always, done posttranslationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies disclosed herein comprises the addition of one or more labels. The term "labeling group" means any detectable label. In some embodiments, the labeling group is coupled to the antibody via spacer arms of various lengths to reduce potential steric hindrance. Various methods for labeling proteins are known in the art and may be used in generating immunoglobulins disclosed herein.

Conjugates

In one embodiment, the coengagement molecules disclosed herein are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the immunoglobulin. Thus, for example, the conjugation of a toxin to an immunoglobulin targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used loosely to convey the broad concept that any immunoglobulin disclosed herein may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs.

In one embodiment, the coengagement molecules disclosed herein are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated entirely by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; plateletgrowth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In yet another embodiment, an coengagement molecules disclosed herein may be conjugated to a "receptor" (such streptavidin) for utilization in tumor pretargeting wherein the immunoglobulin-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the immunoglobulin is conjugated or operably linked to an enzyme in order to employ Antibody Dependent Enzyme Mediated Prodrug Therapy (ADEPT). ADEPT may be used by conjugating or operably linking the immunoglobulin to a prodrug-activating enzyme that converts a prodrug (e.g. a peptidyl chemotherapeutic agent.

When immunoglobulin partners are used as conjugates, conjugate partners may be linked to any region of an immunoglobulin disclosed herein, including at the N- or C-termini, or at some residue in-between the termini. A variety of linkers may find use in immunoglobulins disclosed herein to covalently link conjugate partners to an immunoglobulin. By "linker", "linker sequence", "spacer", "tethering sequence" or grammatical equivalents thereof, herein is meant a molecule or group of molecules (such as a monomer or polymer) that connects two molecules and often serves to place the two molecules in one configuration. Linkers are known in the art; for example, homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. In one embodiment, the linker is from about 1 to 30 amino acids in length, e.g., a linker may be 1 to 20 amino acids in length. Useful linkers include glycine-serine polymers (including, for example, (GS)n, (GSGGS)n (Set forth as SEQ ID NO:43), (GGGGS)n (Set forth as SEQ ID NO:44) and (GGGS)n (Set forth as SEQ ID NO:45), where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxy-alkylenes, or copolymers of polyethylene glycol and polypropylene glycol, may find use as linkers.

Production of Coengagement Molecules

Also disclosed herein are methods for producing and experimentally testing coengagement molecules. The disclosed methods are not meant to constrain embodiments to any particular application or theory of operation. Rather, the provided methods are meant to illustrate generally that one or more immunoglobulins may be produced and experimentally tested to obtain immunoglobulins. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988, all incorporated entirely by reference.

In one embodiment disclosed herein, nucleic acids are created that encode the coengagement molecules, and that may then be cloned into host cells, expressed and assayed, if desired. Thus, nucleic acids, and particularly DNA, may be made that encode each protein sequence. These practices are carried out using well-known procedures. For example, a variety of methods that may find use in generating immunoglobulins disclosed herein are described in Molecular Cloning—A Laboratory Manual, 3$^{rd}$ Ed. (Maniatis, Cold Spring Harbor Laboratory Press, New York, 2001), and Current Protocols in Molecular Biology (John Wiley & Sons), both incorporated entirely by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode immunoglobulins.

The coengagement molecules disclosed herein may be produced by culturing a host cell transformed with nucleic acid, e.g., an expression vector, containing nucleic acid encoding the coengagement molecules, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in generating immunoglobulins disclosed herein are described in the ATCC® cell line catalog, available from the American Type Culture Collection.

In one embodiment, the coengagement molecules are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NSO cells and variants thereof. In an alternate embodiment, library proteins are expressed in bacterial cells. Bacterial expression systems are well known in the art, and include *Escherichia coli* (*E. coli*), *Bacillus subtilis, Streptococcus cremoris*, and *Streptococcus lividans*. In alternate embodiments, immunoglobulins are produced in insect cells (e.g. Sf21/Sf9, *Trichoplusia ni* Bti-Tn5b1-4) or yeast cells (e.g. *S. cerevisiae, Pichia*, etc). In an alternate embodiment, coengagement molecules are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the immunoglobulins may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the coengagement molecules disclosed herein may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating immunoglobulins disclosed herein include but are not limited to those which enable protein expression in mammalian cells, bacteria, insect cells, yeast, and in in vitro systems. As is known in the art, a variety of expression vectors are available, commercially or otherwise, that may find use for expressing coengagement molecules disclosed herein.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the coengagement molecule, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Coengagement molecules may be operably linked to a fusion partner to enable targeting of the expressed protein, purification, screening, display, and the like. Fusion partners may be linked to the immunoglobulin sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS (SEQ ID NO. 44). A fusion partner may be a targeting or signal sequence that directs immunoglobulin and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an immunoglobulin may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen immunoglobulins (see below). Fusion partners that enable a variety of selection methods are well-known in the art. For example, by fusing the members of an immunoglobulin library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, incorporated entirely by reference). Fusion partners may enable immunoglobulins to be labeled. Alternatively, a fusion partner may bind to a specific sequence on the expression vector, enabling the fusion partner and associated immunoglobulin to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, coengagement molecules are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of immunoglobulins disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, immunoglobulins may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, NY, 1994, incorporated entirely by reference. The degree of purification necessary will vary depending on the screen or use of the immunoglobulins. In some instances no purification is necessary. For example in one embodiment, if the immunoglobulins are secreted, screening may take place directly from the media. As is well known in the art, some methods of selection do not involve purification of proteins. Thus, for example, if a library of immunoglobulins is made into a phage display library, protein purification may not be performed.

In Vitro Experimentation

Coengagement molecules may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the immunoglobulins disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of coengagement molecules are screened in an in vitro assay. In vitro assays may allow a broad dynamic range for screening properties of interest. Properties that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of coengagement molecules to a protein or nonprotein molecule that is known or thought to bind the coengagement molecule. In one embodiment, the screen is a binding assay for measuring binding to the target antigen. In an alternate embodiment, the screen is an assay for binding of coengagement molecules to an Fc ligand, including but are not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the immunoglobulin. Assays may employ a variety of detection methods including but not limited to chromogenic, fluorescent, luminescent, or isotopic labels.

The biophysical properties of coengagement molecules, for example stability and solubility, may be tested using a variety of methods known in the art. Protein stability may be determined by measuring the thermodynamic equilibrium between folded and unfolded states. For example, coengagement molecules disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an coengagement molecule may be quantitatively or qualitatively determined using a wide range of methods that are known in the art. Methods which may find use for characterizing the biophysical properties of coengagement molecules disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an immunoglobulin could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the coengagement molecule's stability and solubility.

In one embodiment, coengagement molecules may be tested using one or more cell-based or in vitro assays. For such assays, immunoglobulins, purified or unpurified, are typically added exogenously such that cells are exposed to individual variants or groups of variants belonging to a library. These assays are typically, but not always, based on the biology of the ability of the immunoglobulin to bind to the target antigen and mediate some biochemical event, for example effector functions like cellular lysis, phagocytosis, ligand/receptor binding inhibition, inhibition of growth and/or proliferation, apoptosis and the like. Such assays often involve monitoring the response of cells to immunoglobulin, for example cell survival, cell death, cellular phagocytosis, cell lysis, change in cellular morphology, or transcriptional activation such as cellular expression of a natural gene or reporter gene. For example, such assays may measure the ability of coengagement molecules to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, e.g., humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an immunoglobulin. Cell types for such assays may be prokaryotic or eukaryotic, and a variety of cell lines that are known in the art may be employed. Alternatively, cell-based screens are performed using cells that have been transformed or transfected with nucleic acids encoding the coengagement molecules.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the coengagement molecules disclosed herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the coengagement molecules disclosed herein, a particular challenge arises when using animal models to evaluate the potential for in-human efficacy of candidate polypeptides—this is due, at least in part, to the fact that coengagement molecules that have a specific effect on the affinity for a human Fc receptor may not have a similar affinity effect with the orthologous animal receptor. These problems can be further exacerbated by the inevitable ambiguities associated with correct assignment of true orthologues (Mechetina et al., *Immunogenetics*, 2002 54:463-468, incorporated entirely by reference), and the fact that some orthologues simply do not exist in the animal (e.g. humans possess an FcγRIIa whereas mice do not). Therapeutics are often tested in mice, including but not limited to mouse strains NZB, NOD, BXSB, MRL/lpr, K/BxN and transgenics (including knockins and knockouts). Such mice can develop various autoimmune conditions that resemble human organ specific, systemic autoimmune or inflammatory disease pathologies such as systemic lupus erythematosus (SLE) and rheumatoid arthritis (RA). For example, an immunoglobulin disclosed herein intended for autoimmune diseases may be tested in such mouse models by treating the mice to determine the ability of the immunoglobulin to reduce or inhibit the development of the disease pathology. Because of the incompatibility between the mouse and human Fcγ receptor system, an alternative approach is to use a murine SCID model in which immune deficient mice are engrafted with human PBLs or PBMCs (huPBL-SCID, huPBMC-SCID) providing a semi-functional human immune system with human effector cells and Fc receptors. In such a model, an antigen challenge (such as tetanus toxoid) activates the B cells to differentiate into plasma cells and secrete immunoglobulins, thus reconstituting antigen specific humoral immunity. Therefore, a dual targeting immunoglobulin disclosed herein that specifically binds to IgE and FcγRIIb on B cells may be tested to examine the ability to specifically inhibit B cell differentiation. Such experimentation may provide meaningful data for determination of the potential of said immunoglobulin to be used as a therapeutic. Other organisms, e.g., mammals, may also be used for testing. For example, because of their genetic similarity to humans, monkeys can be suitable therapeutic models, and thus may be used to test the efficacy, toxicity, pharmacokinetics, or other property of the immunoglobulins disclosed herein. Tests of the immunoglobulins disclosed herein in humans are ultimately required for approval as drugs, and thus of course these experiments are contemplated. Thus the immunoglobulins disclosed herein may be tested in humans to determine their therapeutic efficacy, toxicity, pharmacokinetics, and/or other clinical properties.

The coengagement molecules disclosed herein may confer superior performance on Fc-containing therapeutics in animal models or in humans. The receptor binding profiles of such immunoglobulins, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an immunoglobulin with reduced binding to FcγRIIIa, FcγRI and FcγRIIa can be selected to eliminate most cell-mediated effector function, or an immunoglobulin with reduced binding to C1q may be selected to limit complement-mediated effector functions. In some contexts, such effector functions are known to have potential toxic effects. Therefore eliminating them may increase the safety of the Fc-bearing drug and such improved safety may be characterized in animal models. In some contexts, such effector functions are known to mediate the desirable therapeutic activity. Therefore enhancing them may increase the activity or potency of the Fc-bearing drug and such improved activity or potency may be characterized in animal models.

In some embodiments, coengagement molecules disclosed herein may be assessed for efficacy in clinically relevant animal models of various human diseases. In many cases, relevant models include various transgenic animals for specific antigens and receptors.

Relevant transgenic models such as those that express human Fc receptors (e.g., CD32b) could be used to evaluate and test immunoglobulins and Fc-fusions in their efficacy. The evaluation of coengagement molecules by the introduction of human genes that directly or indirectly mediate effector function in mice or other rodents may enable physiological studies of efficacy in autoimmune disorders and RA. Human Fc receptors such as FcγRIIb may possess polymorphisms such as that in gene promoter (−343 from G to C) or transmembrane domain of the receptor 187 I or T which would further enable the introduction of specific and combinations of human polymorphisms into rodents. The various studies involving polymorphism-specific FcRs is not limited to this section, however encompasses all discussions and applications of FcRs in general as specified in throughout this application. Immunoglobulins disclosed herein may confer superior activity on Fc-containing drugs in such transgenic models, in particular variants with binding profiles optimized for human FcγRIIb mediated activity may show superior activity in transgenic CD32b mice. Similar improvements in efficacy in mice transgenic for the other human Fc receptors, e.g. FcγRIIa, FcγRI, etc., may be observed for coengagement molecules with binding profiles optimized for the respective receptors. Mice transgenic for multiple human receptors would show improved activity for immunoglobulins with binding profiles optimized for the corresponding multiple receptors.

Because of the difficulties and ambiguities associated with using animal models to characterize the potential efficacy of candidate therapeutic antibodies in a human patient, some variant polypeptides disclosed herein may find utility as proxies for assessing potential in-human efficacy. Such proxy molecules may mimic—in the animal system—the FcR and/or complement biology of a corresponding candidate human immunoglobulin. This mimicry is most likely to be manifested by relative association affinities between specific immunoglobulins and animal vs. human receptors. For example, if one were using a mouse model to assess the potential in-human efficacy of an Fc variant that has reduced affinity for the inhibitory human FcγRIIb, an appropriate proxy variant would have reduced affinity for mouse FcγRII. It should also be noted that the proxy Fc variants could be created in the context of a human Fc variant, an animal Fc variant, or both.

In one embodiment, the testing of coengagement molecules may include study of efficacy in primates (e.g. cynomolgus monkey model) to facilitate the evaluation of depletion of specific target cells harboring the target antigen. Additional primate models include but are not limited to use of the rhesus monkey to assess Fc polypeptides in therapeutic studies of autoimmune, transplantation and cancer.

Toxicity studies are performed to determine antibody or Fc-fusion related-effects that cannot be evaluated in standard pharmacology profiles, or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated, are evaluated for cross-reactivity with normal tissues, immunogenicity/antibody production, conjugate or linker toxicity and "bystander" toxicity of radiolabelled species. Nonetheless, such studies may have to be individualized to address specific concerns and following the guidance set by ICH S6 (Safety studies for biotechnological products, also noted above). As such, the general principles are that the products are sufficiently well characterized, impurities/contaminants have been removed, that the test material is comparable throughout development, that GLP compliance is maintained.

The pharmacokinetics (PK) of the coengagement molecules disclosed herein may be studied in a variety of animal systems, with the most relevant being non-human primates such as the cynomolgus and rhesus monkeys. Single or repeated i.v./s.c. administrations over a dose range of 6000-fold (0.05-300 mg/kg) can be evaluated for half-life (days to weeks) using plasma concentration and clearance. Volume of distribution at a steady state and level of systemic absorbance can also be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T1/2). Additional measured parameters could include compartmental analysis of concentration-time data obtained following i.v. administration and bioavailability.

The coengagement molecules disclosed herein may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of coengagement molecules disclosed herein. Because coengagement molecules of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific cells or blocking signaling mechanisms, measuring inhibition of antigen-specific antibodies etc. The coengagement molecules disclosed herein may target particular effector cell populations and thereby direct Fc-containing drugs to induce certain activities to improve potency or to increase penetration into a particularly favorable physiological compartment. For example, neutrophil activity and localization can be targeted by an coengagement molecule that targets FcγRIIIb. Such pharmacodynamic effects may be demonstrated in animal models or in humans.

Use

Once made the coengagement molecules as described herein find use in a variety of methods. In a preferred embodiment the method includes contacting a cell that coexpresses IgE and FcγRIIb with a coengagement molecule such that both IgE and FcγRIIb are bound by the coengagement molecule and the cell is inhibited. By "inhibited" in this context is meant that the coengagement molecule is preventing or reducing activation and/or proliferation of IgE+ B cells.

The coengagement molecules disclosed herein may find use in a wide range of products. In one embodiment an coengagement molecule disclosed herein is a therapeutic, a diagnostic, or a research reagent. The coengagement molecules may find use in a composition that is monoclonal or polyclonal. The coengagement molecules disclosed herein may be used for therapeutic purposes. As will be appreciated by those in the art, the coengagement molecules disclosed herein may be used for any therapeutic purpose that antibodies, and the like may be used for. The coengagement molecules may be administered to a patient to treat disorders including but not limited to autoimmune and inflammatory diseases, infectious diseases, and cancer.

A "patient" for the purposes disclosed herein includes both humans and other animals, e.g., other mammals. Thus the coengagement molecules disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an coengagement molecule prior to onset of the disease results in treatment of the disease. As another example, successful administration of an optimized coengagement molecule after clinical manifestation of the disease to combat the symptoms of the disease comprises treatment of the disease. "Treatment" and "treating" also encompasses administration of an optimized immunoglobulin after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an coengagement molecule disclosed herein is administered to a patient having a disease involving inappropriate expression of a protein or other molecule. Within the scope disclosed herein this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the immunoglobulins disclosed herein.

Disclosed herein are novel methods of treating IgE-mediated disorders, e.g., food and environmental allergies and allergic asthma. In preferred embodiments, allergic diseases that may be treated by the products and methods of the invention include allergic and atopic asthma, atopic dermatitis and eczema, allergic rhinitis, allergic conjunctivitis and rhinoconjunctivitis, allergic encephalomyelitis, allergic rhinitis, allergic vasculitis, and anaphylactic shock. Environmental and food allergies that may be treated include allergies to dustmite, cockroach, cat and other animals, pollen (including ragweed, Bermuda grass, Russian thistle, oak, rye, and others), molds and fungi (e.g., *Alternaria alternata, Aspergillus* and others), latex, insect stings (bee, wasp, and others), penicillin and other drugs, strawberries and other fruits and vegetables, peanuts, soy, and other legumes, walnuts and other treenuts, shellfish and other seafood, milk and other dairy products, wheat and other grains, and eggs. Indeed, any food allergen, aeroallergen, occupational allergen, or other IgE-mediated environmental allergen may be treated by a therapeutic amount of the products disclosed in this invention. For examples of common allergens, see Arbes et al., *Prevalences of positive skin test responses to* 10 *common allergens in the US population: Results from the Third National Health and Nutrition Examination Survey*, Clinical Gastroenterology 116(2), 377-383 (2005).

Also disclosed are diagnostic tests to identify patients who are likely to show a favorable clinical response to an coengagement molecule disclosed herein, or who are likely to exhibit a significantly better response when treated with an coengagement molecule disclosed herein versus one or more currently used therapeutics. Any of a number of methods for determining FcγR polymorphisms in humans known in the art may be used. Furthermore, also disclosed are prognostic tests performed on clinical samples such as blood and tissue samples. Such tests may assay for activity, regardless of mechanism. Such information may be used to identify patients for inclusion or exclusion in clinical trials, or to inform decisions regarding appropriate dosages and treatment regimens. Such information may also be used to select a drug that contains a particular coengagement molecule that shows superior activity in such assay.

Formulation

Pharmaceutical compositions are contemplated wherein an coengagement molecule disclosed herein and one or more therapeutically active agents are formulated. Formulations of the coengagement molecules disclosed herein are prepared for storage by mixing said immunoglobulin having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In one embodiment, the pharmaceutical composition that comprises the immunoglobulin disclosed herein may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Some embodiments include at least one of the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration may be sterile. This is readily accomplished by filtration through sterile filtration membranes or other methods.

The coengagement molecules disclosed herein may also be formulated as immunoliposomes. A liposome is a small vesicle comprising various types of lipids, phospholipids and/or surfactant that is useful for delivery of a therapeutic agent to a mammal. Liposomes containing the immunoglobulin are prepared by methods known in the art. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The coengagement molecule and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an coengagement molecule disclosed herein, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the immunoglobulin may be directly applied as a solution or spray. As is known in the art, the pharmaceutical composition may be formulated accordingly depending upon the manner of introduction.

Subcutaneous administration may be used in circumstances where the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. Antibodies disclosed herein may be more amenable to subcutaneous administration due to, for example, increased potency, improved serum half-life, or enhanced solubility.

As is known in the art, protein therapeutics are often delivered by IV infusion or bolus. The antibodies disclosed herein may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Antibodies disclosed herein may be more amenable to intrapulmonary delivery. FcRn is present in the lung, and may promote transport from the lung to the bloodstream (e.g. Syntonix WO 04004798, Bitonti et al. (2004) Proc. Nat. Acad. Sci. 101:9763-8, both incorporated entirely by reference). Accordingly, antibodies that bind FcRn more effectively in the lung or that are released more efficiently in the bloodstream may have improved bioavailability following intrapulmonary administration. Antibodies disclosed herein may also be more amenable to intrapulmonary administration due to, for example, improved solubility or altered isoelectric point.

Furthermore, coengagement molecules disclosed herein may be more amenable to oral delivery due to, for example, improved stability at gastric pH and increased resistance to proteolysis. Furthermore, FcRn appears to be expressed in the intestinal epithelia of adults, so antibodies disclosed herein with improved FcRn interaction profiles may show enhanced bioavailability following oral administration. FcRn mediated transport of antibodies may also occur at other mucus membranes such as those in the gastrointestinal, respiratory, and genital tracts.

In addition, any of a number of delivery systems are known in the art and may be used to administer the antibodies disclosed herein. Examples include, but are not limited to, encapsulation in liposomes, microparticles, microspheres (e.g., PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the Lupron Depot®, and poly-D-(–)-3-hydroxy-buryric acid. It is also possible to administer a nucleic acid encoding an immunoglobulin disclosed herein, for example by retroviral infection, direct injection, or coating with lipids, cell surface receptors, or other transfection agents. In all cases, controlled release systems may be used to release the immunoglobulin at or close to the desired location of action.

Dosing

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active coengagement molecule in the formulation may vary from about 0.1 to 100 weight %. In one embodiment, the concentration of the coengagement molecule is in the range of 0.003 to 1.0 molar. In order to treat a patient, a therapeutically effective dose of the immunoglobulin disclosed herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight. In one embodiment, dosages range from 1 to 10 mg/kg.

In some embodiments, only a single dose of the coengagement molecule is used. In other embodiments, multiple doses of the coengagement molecule are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the coengagement molecules disclosed herein are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the coengagement molecules disclosed herein and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The coengagement molecules disclosed herein may be administered concomitantly with one or more other therapeutic regimens or agents. Additional therapeutic regimes or agents may be used to treat the same disease, to treat an accompanying complication, or may be used to improve the efficacy or safety of the immunoglobulin Particularly preferred co-therapies include those that are approved or are being clinically evaluated for the treatment of IgE-mediated disorders such as allergies and asthma. In particular, the therapeutic compositions of the invention may be used in combination with anti-inflammatories such as corticosteroids, and/or brochodilators such as inhaled β2-agonists, the two major groups of medications. Inhaled corticosteroids include fluticasone, budesonide, flunisolide, mometasone, triamcinolone, and beclomethasone, whereas oral corticosteroids include prednisone, methylprednisolone, and prednisolone. Other steroids include glucocorticoids, dexamethasone, cortisone, hydroxycortisone, azulfidine-icosanoids such as prostaglandins, thromboxanes, and leukotrienes, as well as topical steroids such as anthralin, calcipotriene, clobetasol, and tazarotene. Bronchodilators increase the diameter of the air passages and ease the flow to and from the lungs. Brochodilators that may be combined with the therapies of the invention include short-acting bronchodilators such as metaproterenol, ephedrine, terbutaline, and albuterol, and long-acting bronchodilators such as salmeterol, metaproterenol, and theophylline.

The therapies of the invention may be combined with non-steroidal anti-inflammatory drugs (NSAIDs) such as asprin, ibuprofen, celecoxib, diclofenac, etodolac, fenoprofen, indomethacin, ketoralac, oxaprozin, nabumentone, sulindac, tolmentin, rofecoxib, naproxen, ketoprofen, and nabumetone. Co-therapies may include antihistamines such as loratadine, fexofenadine, cetirizine, diphenhydramine, chlorpheniramine maleate, clemastine, and azelastine. Co-therapy may include cromoglycate, cromolyn sodium, and nedrocromil, as well as decongestants, spray or oral, such as oxymetazoline, phenylephrine, and pseudoephedrine. The therapies of the invention may be combined with a class of anti-inflammatories called leukotriene-receptor antagonists such as pranlukast, zafirlukast, and montelukast, and leukotriene-receptor synthesis-inhibitors such as zileuton.

The therapies of the invention may be combined with other immunotherapies, including allergy shots, as well as other antagonists of IgE or FcεRs. The therapies of the invention may be combined with antagonists of chemokines or cytokines, including but not limited to antibodies and Fc fusions, including but not limited to inhibitors of chemokines CCR3, CCR4, CCR8, and CRTH2, and CCR5, and inhibitors of cytokines IL-13, IL-4, IL-5, IL-6, IL-9, IL-10, IL-12, IL-15, IL-18, IL-19, IL-21, Class II family of cytokine receptors, IL-22, IL-23, IL-25, IL-27, IL-31, and IL-33. The therapies of the invention may be combined with modulators of adhesion, transcription factors, and/or intracellular signalling. For example, the immunoglobulins of the invention may be combined with modulators of NF-κb, AP-1, GATA-3, Stat1, Stat-6, c-maf, NFATs, suppressors of cytokine signaling (SOCS), peroxisome proliferator-activated receptors (PPARs), MAP kinase, p38 MAPK, JNK, and sphingosine I-phosphate receptors. The therapies of the invention may be administered with suplatast tolilate, inhibitors of phosphodiesterase 4 (PDE4), calcium channel blockers, and heparin-like molecules. Possible co-therapies for the invention are described further in detail in Caramori et al., 2008, Journal of Occupational Medicine and Toxicology 3-S1-S6.

The therapies of the invention may also be used in conjuction with one or more antibiotics, anti-fungal agents, or anti-viral agents. The antibodies disclosed herein may also be combined with other therapeutic regimens such as surgery.

EXAMPLES

Examples are provided below are for illustrative purposes only. These examples are not meant to constrain any embodiment disclosed herein to any particular application or theory of operation.

Example 1

Novel Methods for Inhibiting IgE+ FcγRIIb+ Cells

Immunoglobulin IgE is a central initiator and propagator of allergic response in affected tissue. IgE binds the high affinity receptor for IgE (FcεRI), a key receptor involved in immediate allergic manifestations that is expressed on a variety of effector cells, including mast cells, basophils, eosinophils, as well as the cell types. Cross-linking of FcεRI by immune-complexed IgE-allergen activates these cells, releasing chemical mediators such as histamine, prostaglandins, and leukotrienes, which may lead to the development of a type I hypersensitivity reaction. The approved monoclonal antibody Omalizumab (Xolair) neutralizes IgE by binding to it and blocking engagement with FcεR's. Omalizumab reduces bioactive IgE through sequestration, attenuating the amount of antigen-specific IgE that can bind to and sensitize tissue mast cells and basophils. This neutralization of free circulating IgE, in turn, leads to a decrease in symptoms of allergic diseases. Interestingly, serum IgE levels increase after start of therapy because of omalizumab-IgE complex formation and may remain high up to a year after stopping therapy. Consequently, this issue may lead to false-negatives on diagnostic tests and therefore IgE levels must be routinely checked.

A novel approach to targeting the IgE pathway involves not only blocking free circulating IgE from engaging FcεRs on effector cells, but targeting the source of IgE production. IgE is secreted by IgE-producing plasma cells located in lymph nodes draining the site of antigen entry or locally at the sites of allergic reactions. IgE-producing plasma cells are differentiated from IgE+ B cells. Class switching of B cells to IgE production is induced by two separate signals, both of which can be provided by TH2 cells.

There are two forms of immunoglobulins: the secreted and the membrane-anchored form. The membrane-anchored form differs from the secreted form in that the former has a membrane-anchoring peptide extending from the C terminus of the heavy-chain. Membrane-anchored immunoglobulin on B-cells, also referred to as the B cell receptor (BCR) complex, is critical for B-cell functions. It can transduce signals for resting B cells to differentiate into activated lymphoblasts and Ig-secreting plasma cells.

Differentiated B cells expressing membrane-anchored IgE, referred to here as mIgE+ B cells, possess a natural negatively regulating feedback mechanism—the inhibitory Fc receptor FcγRIIb. FcγRIIb is expressed on a variety of immune cells, including B cells, dendritic cells, monocytes, and macrophages, where it plays a critical role in immune regulation. In its normal role on B cells, FcγRIIb serves as a feedback mechanism to modulate B cell activation through the B cell receptor (BCR). Engagement of BCR by immune complexed antigen on mature B cells activates an intracellular signaling cascade, including calcium mobilization, which leads to cell proliferation and differentiation. However, as IgG antibodies with specificity to the antigen are produced, the associated immune complexes (ICs) can crosslink the BCR with FcγRIIb, whereupon the activation of BCR is inhibited by engagement of FcγRIIb and associated intracellular signaling pathways that interfere with the downstream pathways of BCR activation. The expression of FcγRIIb on the surface of mIgE+ B cells, which use mIgE as their BCR, serves as a negative regulator of these cell types.

A novel strategy for inhibiting IgE-mediated disease, illustrated in FIG. 1, is to inhibit IgE+ B cells (i.e. B cells expressing membrane anchored IgE) by coengaging membrane anchored IgE and the inhibitory receptor FcγRIIb. In B cells that have class-switched to express IgE, mIgE serves as the BCR (referred to herein as mIgE BCR). This approach would potentially mimic the natural biological mechanism of immune complex-mediated suppression of B cell activation, thereby preventing differentiation into IgE-producing plasma cells. IgE-producing plasma cells reside in the bone marrow and probably have a life span of several weeks to several months. Since new IgE-secreting plasma cells go through mIgE-expressing B-cell stages during differentiation, if their generation is abrogated by inhibiting their mIgE+ B cell precursors with this anti-IgE treatment, the existing plasma cells will die off within weeks to months, and thus the production of IgE will also gradually abate. Importantly, inhibition of IgE+ memory B cells, which bear mIgE, would also be inhibited by anti-IgE immunoglobulins that coengage FcγRIIb with high affinity. If this occurs, therapy may have long-term impact on the fundamental disease.

Example 2

Anti-IgE Antibodies with High Affinity for FcγRIIb

Under physiological conditions, bridging of the BCR with FcγRIIb and subsequent B cell suppression occurs via immune complexes of IgGs and cognate antigen. The design strategy was to reproduce this effect using a single crosslinking antibody. Human IgG binds human FcγRIIb with weak affinity (greater than 100 nM for IgG1), and FcγRIIb-mediated inhibition occurs in response to immune-complexed but not monomeric IgG. It was reasoned that high affinity to this receptor (less than 100 nM) would be required for maximal inhibition of B cell activation. In order to enhance the inhibitory activity of the anti-IgE antibodies of the invention, the Fc region was engineered with variants that improve binding to FcγRIIb. Engineered Fc variants have been described that bind to FcγRIIb with improved affinity relative to native IgG1 (U.S. Ser. No. 12/156,183, filed May 30, 2008, entitled "Methods and Compositions for Inhibiting CD32b Expressing cells", herein incorporated expressly by reference).

Variants were originally generated in the context of an antibody targeting the antigen CD19, a regulatory component of the BCR coreceptor complex. The Fv region of this antibody is a humanized and affinity matured version of antibody 4G7, and is referred to herein as HuAM4G7. The Fv genes for this antibody were subcloned into the mammalian expression vector pTT5 (National Research Council Canada). Mutations in the Fc domain were introduced using site-directed mutagenesis (QuikChange, Stratagene, Cedar Creek, Tex.). In addition, control knock out variants with ablated affinity for Fc receptors were generated that comprise the substitutions G236R and L328R (G236R/L328R). This variant is referred to as Fc-KO or Fc knockout. Heavy and light chain constructs were cotransfected into HEK293E cells for expression, and antibodies were purified using protein A affinity chromatography (Pierce Biotechnology, Rockford, Ill.).

Recombinant human FcγRIIb protein for binding studies was obtained from R&D Systems (Minneapolis, Minn.). Genes encoding FcγRIIa and FcγRIIIa receptor proteins were obtained from the Mammalian Gene Collection (ATCC), and subcloned into pTT5 vector (National Research Council Canada) containing 6×His tags. Allelic forms of the receptors (H131 and R131 for FcγRIIa and V158 and F158 for FcγRIIIa) were generated using QuikChange mutagenesis. Vectors encoding the receptors were transfected into HEK293T cells, and proteins were purified using nickel affinity chromatography.

Variants were tested for receptor affinity using Biacore technology, also referred to as Biacore herein, a surface plasmon resonance (SPR) based technology for studying biomolecular interactions in real time. SPR measurements were performed using a Biacore 3000 instrument (Biacore, Piscataway, N.J.). A protein NG (Pierce Biotechnology) CM5 biosensor chip (Biacore) was generated using a standard primary amine coupling protocol. All measurements were performed using HBS-EP buffer (10 mM HEPES pH 7.4, 0.15 M NaCl, 3 mM EDTA, 0.005% vol/vol surfactant P20, Biacore). Antibodies at 20 nM or 50 nM in HBS-EP buffer were immobilized on the protein NG surface and FcγRs were injected. After each cycle, the surface was regenerated by injecting glycine buffer (10 mM, pH 1.5). Data were processed by zeroing time and response before the injection of FcγR and by subtracting appropriate nonspecific signals (response of reference channel and injection of running buffer). Kinetic analyses were performed by global fitting of binding data with a 1:1 Langmuir binding model using BIAevaluation software (Biacore).

Figure 2:
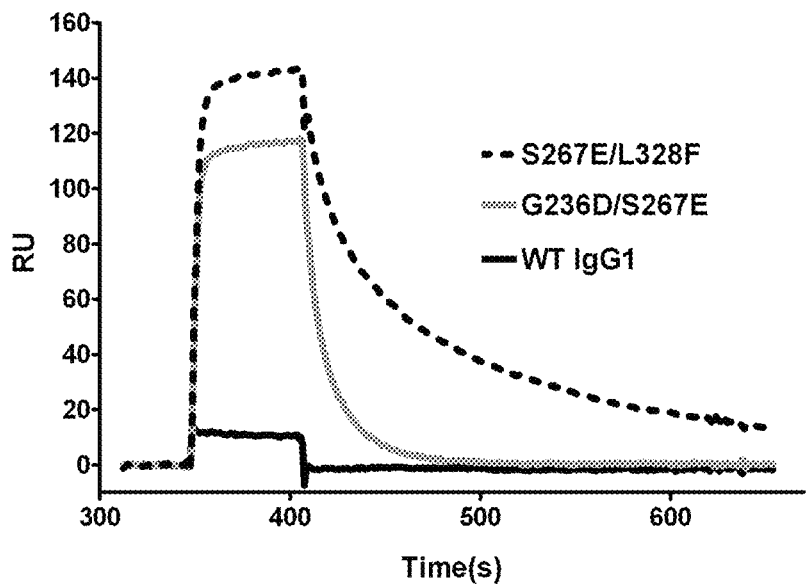
FIG. 2. Biacore surface plasmon resonance sensorgrams showing binding of Fc variant anti-CD19 antibodies to human FcγRIIb.
Figure 3:
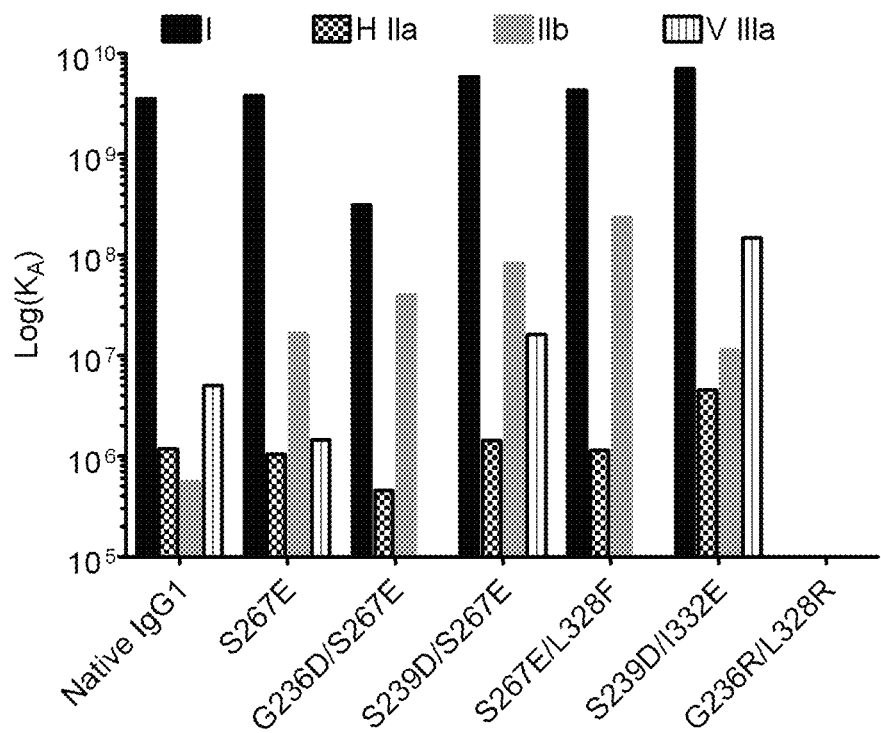
FIG. 3. Affinities of Fc variant antibodies for human FcγRs as determined by Biacore. The graph shows the log(K_A) for binding of variant and WT IgG1 antibodies to human FcγRI (I), H131 FcγRIIa (H IIa), FcγRIIb (IIb), and V158 FcγRIIIa (V IIIa). Binding of G236D/S267E and S267E/L328F to V158 FcγRIIIa was not detectable. Binding of G236R/L328R (Fc-KO) to all receptors tested was not detectable.

A representative set of sensorgrams for binding of select variant anti-CD19 antibodies to FcγRIIb is shown in FIG. 2. The affinities of all variants and WT (native) IgG1 to all of the FcγRs, obtained from fits of the Biacore binding data, are plotted in FIG. 3 and provided numerically in FIG. 4. Whereas WT IgG1 Fc binds with FcγRIIb with μM affinity ($K_D$=1.8 uM in FIG. 4), a number of variants, for example G236D/S267E, S239D/S267E, and S267E/L328F, have been engineered that bind the inhibitory receptor more tightly. The S239D/I332E variant, as described in U.S. Ser. No. 11/124,620, also has improved affinity for the activating receptors FcγRIIa and FcγRIIIa, and therefore is capable of mediated enhanced antibody-dependent cell-mediated cytotoxicity (ADCC) and phagocytosis (ADCP). The G236R/L328R variant, also referred to Fc-knockout or Fc-KO, lacks binding to the Fc receptors, and is used as a control in the experiments described herein.

Select variants were constructed in antibodies that target IgE. The heavy and light chain variable regions (VH and VL) of anti-IgE antibodies are provided in FIG. 5. Omalizumab is a humanized antibody that is currently approved for the treatment of allergic asthma, and is marketed under the name Xolair. MaE11 is the murine precursor of Omalizumab. H1L1_MaE11 is a novel humanized version of MaE11. Genes encoding the heavy and light VH and VL domains of these anti-IgE antibodies were synthesized commercially (Blue Heron Biotechnologies). Also synthesized were the variable region VH and VL genes of the anti-respiratory syncytial virus (RSV) antibody motavizumab, used in the experiments described herein as a negative control. VL genes were subcloned into the mammalian expression vector pTT5 (NRC-BRI, Canada) encoding the Ckappa constant chain. VH genes were subcloned into the pTT5 vector encoding native IgG1 and variant constant chains. Amino acid sequences of select constant chains are provided in FIG. 6. All DNA was sequenced to confirm the fidelity of the sequences. The amino acid sequences of the full length heavy and light chains of select antibodies are provided in FIG. 7.

Plasmids containing heavy and light chain genes were co-transfected into HEK293E cells using lipofectamine (Invitrogen) and grown in FreeStyle 293 media (Invitrogen). After 5 days of growth, the antibodies were purified from the culture supernatant by protein A affinity using MabSelect resin (GE Healthcare).

Figures 8, 9:
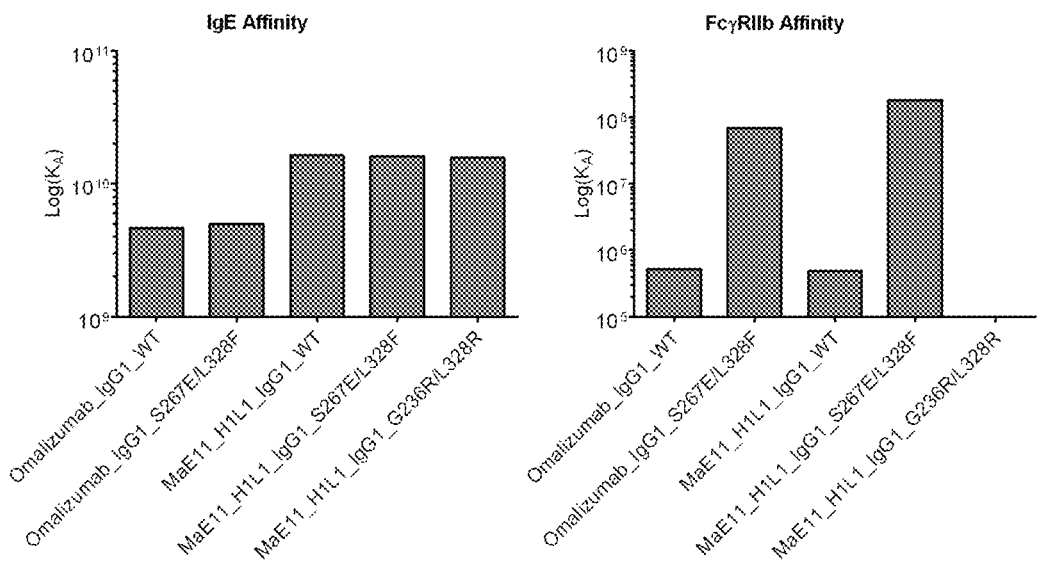
FIG. 8. Table of affinity data for binding of WT and variant anti-IgE antibodies to the IgE Fc region and FcγRIIb.
FIG. 9. Plot of affinity data for binding of WT and variant anti-IgE antibodies to the IgE Fc region and FcγRIIb.

Variant and native IgG1 anti-IgE antibodies were tested for binding to IgE and to FcγRIIb using Biacore. DNA encoding the Fc region of IgE, which contains the binding site for the anti-IgE antibodies used, was synthesized (Blue Heron Biotechnologies) and subcloned into the pTT5 vector. IgE Fc was expressed in 293E cells and purified using protein A as described above. SPR measurements were performed using the protein A/antibody capture method described above, except that analyte was either FcγRIIb or the Fc region of IgE. Data acquisition and fitting are as described above. FIG. 8 provides the resulting equilibrium binding constants ($K_D$s) obtained from these binding experiments, as well as the fold affinity relative to native IgG1 for binding to FcγRIIb. FIG. 9 shows plots of these data. The results confirm the high of affinity of the antibodies for IgE, and that the S267E/L328F variant improves binding to FcγRIIb over two orders of magnitude, consistent with previous results.

The use of particular variants, for example S267E/L328F and S239D/I332E, are meant here as proof of concept for the mechanism as described herein, and are not meant to constrain the invention to their particular use. The data provided in U.S. Ser. No. 12/156,183 and U.S. Ser. No. 11/124,620 indicate that a number of engineered variants, at specific Fc positions, provide the targeted properties. Substitutions to enhance FcγR affinity, in particular to FcγRIIb, include: 234, 235, 236, 237, 239, 266, 267, 268, 325, 326, 327, 328, and 332. In some embodiments, substitutions are made to at least one or more of the nonlimiting following positions to enhance affinity to FcγRIIb: 235, 236, 239, 266, 267, 268, and 328.

Nonlimiting combinations of positions for making substitutions to enhance affinity to FcγRIIb include: 234/239, 234/267, 234/328, 235/236, 235/239, 235/267, 235/268, 235/328, 236/239, 236/267, 236/268, 236/328, 237/267, 239/267, 239/268, 239/327, 239/328, 239/332, 266/267, 267/268, 267/325, 267/327, 267/328, 267/332, 268/327, 268/328, 268/332, 326/328, 327/328, and 328/332. In some embodiments, combinations of positions for making substitutions to enhance affinity to FcγRIIb include, but are not limited to: 235/267, 236/267, 239/268, 239/267, 267/268, and 267/328.

Substitutions for enhancing affinity to FcγRIIb include: 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. In some embodiments, combination of positions for making substitutions for enhancing affinity to FcγRIIb include, but are not limited to: 235Y, 236D, 239D, 266M, 267E, 268D, 268E, 328F, 328W, and 328Y.

Combinations of substitutions for enhancing affinity to FcγRIIb include: L234D/S267E, L234E/S267E, L234F/S267E, L234E/L328F, L234W/S239D, L234W/S239E, L234W/S267E, L234W/L328Y, L235D/S267E, L235D/L328F, L235F/S239D, L235F/S267E, L235F/L328Y, L235Y/G236D, L235Y/S239D, L235Y/S267D, L235Y/S267E, L235Y/H268E, L235Y/L328F, G236D/S239D, G236D/S267E, G236D/H268E, G236D/L328F, G236N/S267E, G237D/S267E, G237N/S267E, S239D/S267D, S239D/S267E, S239D/H268D, S239D/H268E, S239D/A327D, S239D/L328F, S239D/L328W, S239D/L328Y, S239D/I332E, S239E/S267E, V266M/S267E, S267D/H268E, S267E/H268D, S267E/H268E, S267E/N325L, S267E/A327D, S267E/A327E, S267E/L328F, S267E/L328I, S267E/L328Y, S267E/I332E, H268D/A327D, H268D/L328F, H268D/L328W, H268D/L328Y, H268D/

I332E, H268E/L328F, H268E/L328Y, A327D/L328Y, L328F/I332E, L328W/I332E, and L328Y/I332E. In some embodiments, combinations of substitutions for enhancing affinity to FcγRIIb include, but are not limited to: L235Y/S267E, G236D/S267E, S239D/H268D, S239D/S267E, S267E/H268D, S267E/H268E, and S267E/L328F.

Example 3

In Vitro Inhibition of IgE+ B Cells by Anti-IgE Antibodies with High Affinity to FcγRIIb An enzyme-linked immunosorbent assay (ELISA) was established to detect IgE. Flat bottom plates were prepared by coating with pH 9.4 NaBicarbonate buffer, followed by adherance with anti-IgE capture antibodies at 10 ug/ml overnight in pH 9.4 (0.1 M NaBicarbonate buffer). After overnight, the plate was blocked with 3% BSA/PBS, and serial dilutions of IgE (from a human IgE ELISA kit, Bethyl Laboratories) was added 3× to 1 ug/ml. After 3 hours, plates were washed 3× (200 ul) with TTBS, and bound IgE was measured. HRP-conjugated goat polyclonal anti-human IgE antibody (Bethyl Laboratories) was added at (1:5000) for 1 hour in 1% BSA/PBS. Samples were washed 3× and IgE was detected with TMB peroxidase substrate (KPL, Inc 50-76-00). Reactions were stopped with 50 ul 2N H2SO4 and read at 450 nm.

Figure 10:
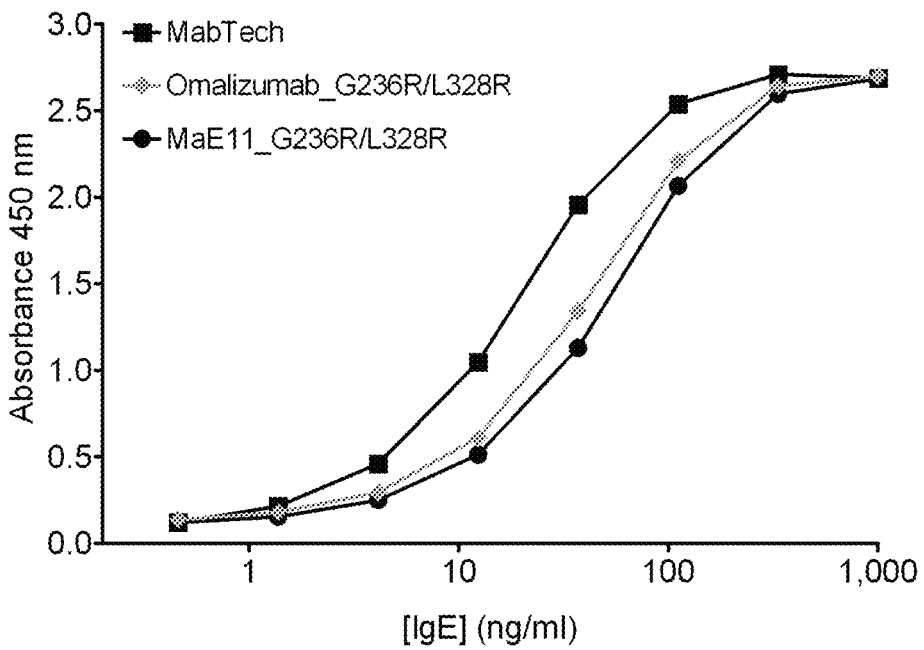
FIG. 10. IgE ELISA using commercial (MabTech) and in-house (Omalizumab and MaE11) anti-IgE antibodies as capture reagents.
Figure 11:
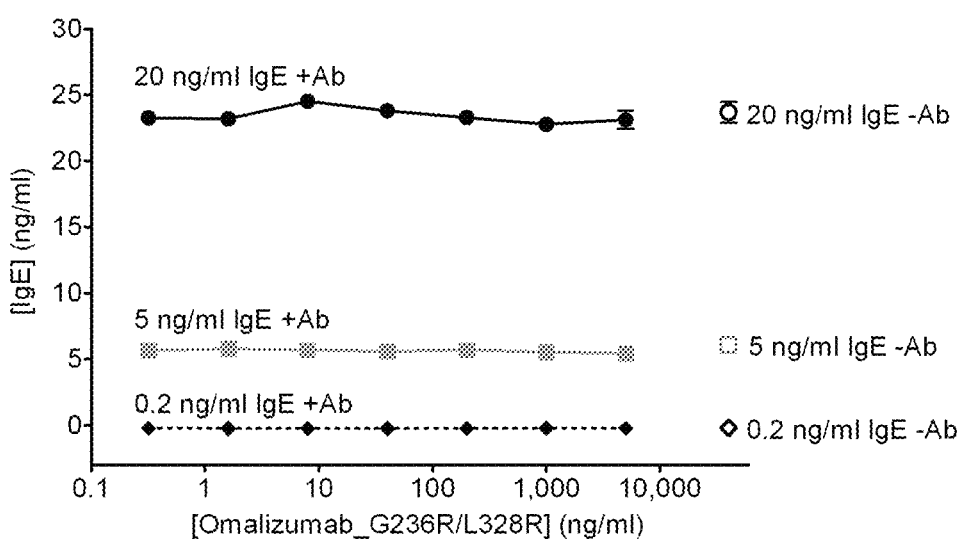
FIG. 11. The variable region of the anti-IgE antibody omalizumab does not compete with MabTech capture antibody for IgE detection in the ELISA protocol.

FIG. 10 shows capture of IgE with various anti-human IgE antibodies, including a pool of three monoclonal anti-IgE antibodies (MabTech; 107/182/101), MaE11_IgG1_G236R/L328R, and Omalizumab_IgG1_G236R/L328R. The data show that the commercial anti-IgE antibody reagent (MabTech), Omalizumab, and its parent chimeric antibody MaE11 are able to capture IgE. In order to use this assay to detect IgE, it was necessary to determine whether MaE11 and omalizumab antibodies would interfere with IgE capture by the MabTech anti-IgE reagent. The assay was repeated as described above, and concentration of IgE from absorbance was calculated using a standard curve. FIG. 11 shows that anti-IgE antibody omalizumab_G236R/L328R does not compete with the MabTech anti-IgE antibody in the current ELISA protocol.

Figure 12:
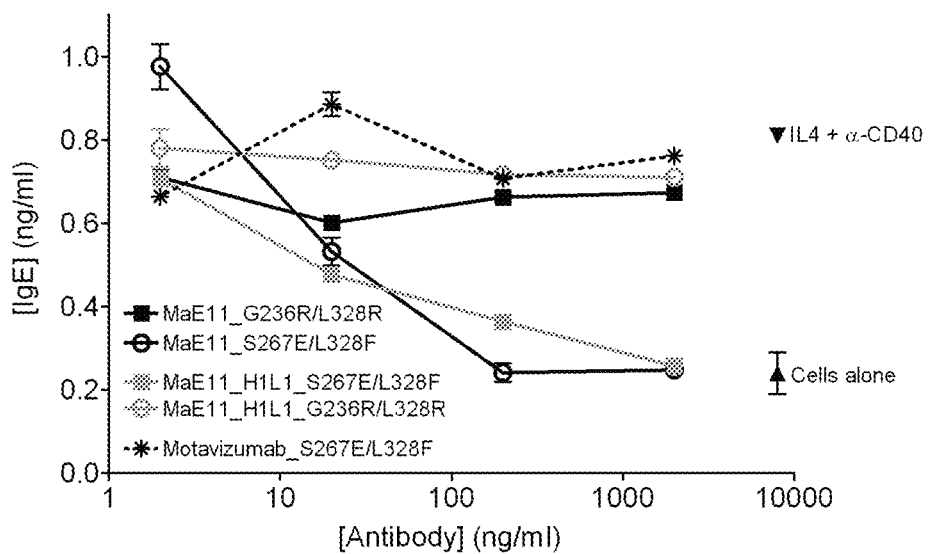
FIG. 12. Inhibition of class-switched IgE+ B cells with variant anti-IgE antibodies enhanced for FcγRIIb affinity, but not antibodies lacking FcγR binding (Fc variant G236R/L328R) or lacking binding to IgE (motavizumab). The plot shows the concentration of IgE released from PBMCs after 12 days incubation with IL-4, anti-CD40 (α-CD40) agonist antibody, and varying concentrations of the antibodies shown.
Figure 13:
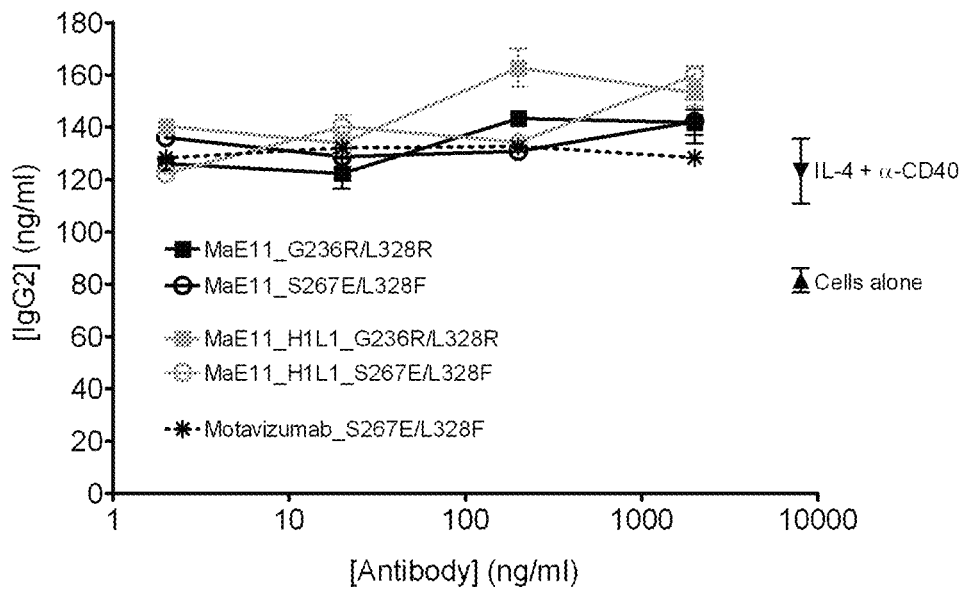
FIG. 13. Variant anti-IgE antibodies do not inhibit class-switched IgG2+ B cells. The plot shows the concentration of IgG2 released from PBMCs after 12 days incubation with IL-4, α-CD40, and varying concentrations of the antibodies shown.
Figure 14:
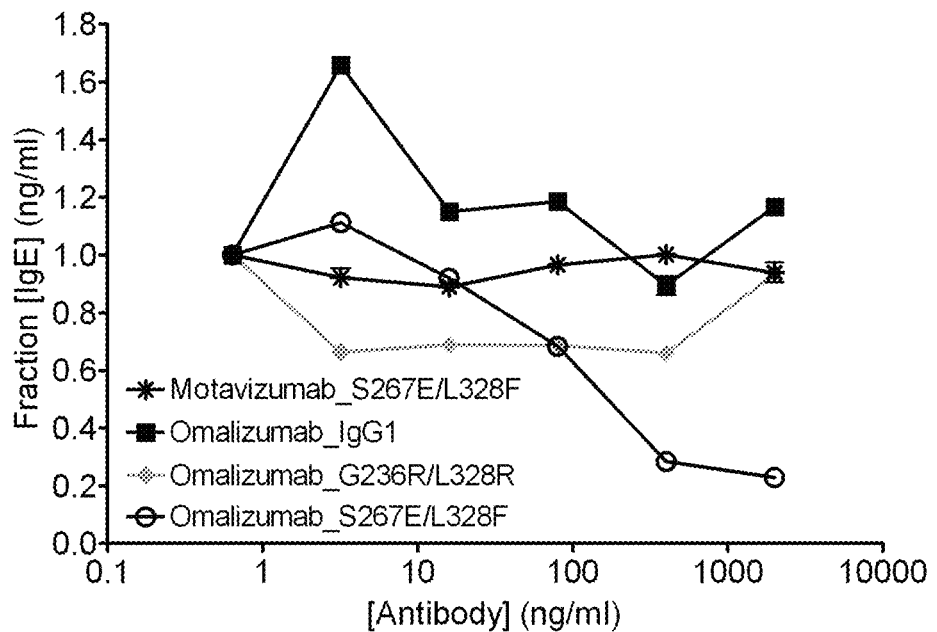
FIG. 14. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, and varying concentrations of the antibodies shown. Data were normalized to the lowest concentration of antibody.

Fc variant anti-IgE antibodies were tested for their capacity to inhibit IgE+ B cells. Human PBMCs were induced to class switch to IgE producing B cells by adding 5 ng/ml interleukin-4 (IL-4) and 100 ng/ml anti-CD40 antibody (clone G28.5 IgG1). The anti-CD40 antibody is an agonist of CD40, and thus mimics the activity of the co-activator CD40L. Varying concentration of anti-IgE antibodies were added, and the samples were incubated for 12 days. ELISA plates were prepared and blocked as described above, using 5 ug/ml Mabtech anti-IgE as the capture antibody. 100 ul of the PBMC samples were added and incubated >3 hours, and then washed with TTBS 3× (200 ul). Antibody-HRP conjugated antibody was added and detected as described above. Absorbance at 450 nm was converted to IgE concentration using a standard curve. The results are shown in FIG. 12. Antibodies lacking FcγR binding (G236R/L328R variants) or having no specificity for IgE (Motavizumab anti-RSV antibody) had no effect on IgE production from differentiated B cells. In contrast, variant antibodies with greater affinity for FcγRIIb inhibited IgE production. These data suggest that co-engagement of surface IgE and the inhibitory FcγR receptor FcγRIIb inhibits class-switched B cells of that immunoglobulin type. Inhibition of IgE+ B cells reduces the number of IgE expressing plasma cells, which in turn reduces the amount of IgE detected. To evaluate the selectivity of this activity for IgE producing B cells, human IgG2 was measured from the same samples using an IgG2 ELISA (Bethyl Laboratories). FIG. 13 shows that IgG2 secretion was not inhibited, indicating that the inhibitory activity of anti-IgE antibodies with high FcγRIIb affinity is selective for IgE+ class-switched cells. Repeat of this experiment using variant versions of the approved anti-IgE antibody Omalizumab showed similar inhibitory results by the variant with high FcγRIIb affinity (FIG. 14).

Figure 15:
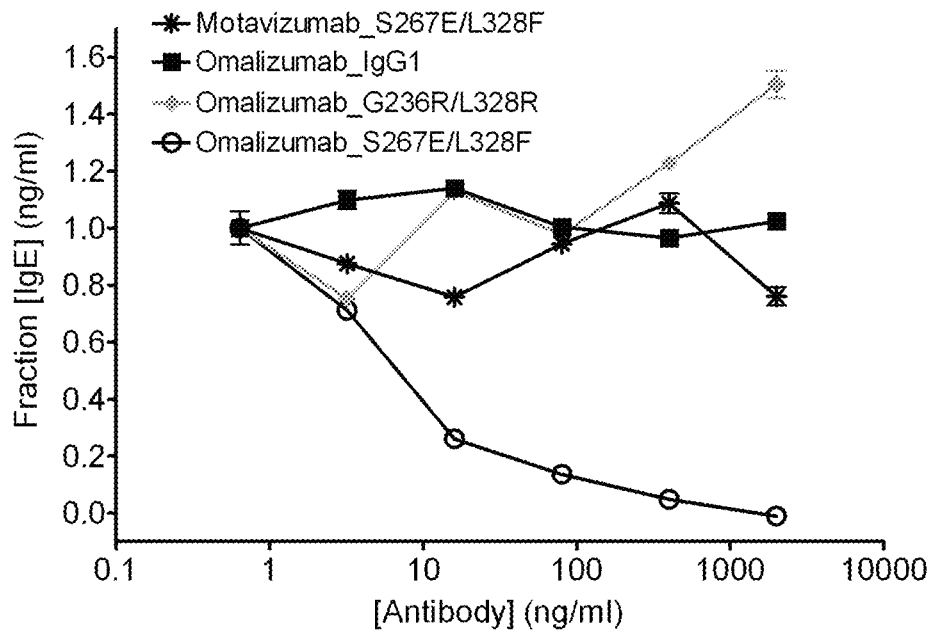
FIG. 15. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, anti-CD79b BCR cross-linking antibody, and varying concentrations of the antibodies shown. Data were normalized to the lowest concentration of antibody.
Figure 16:
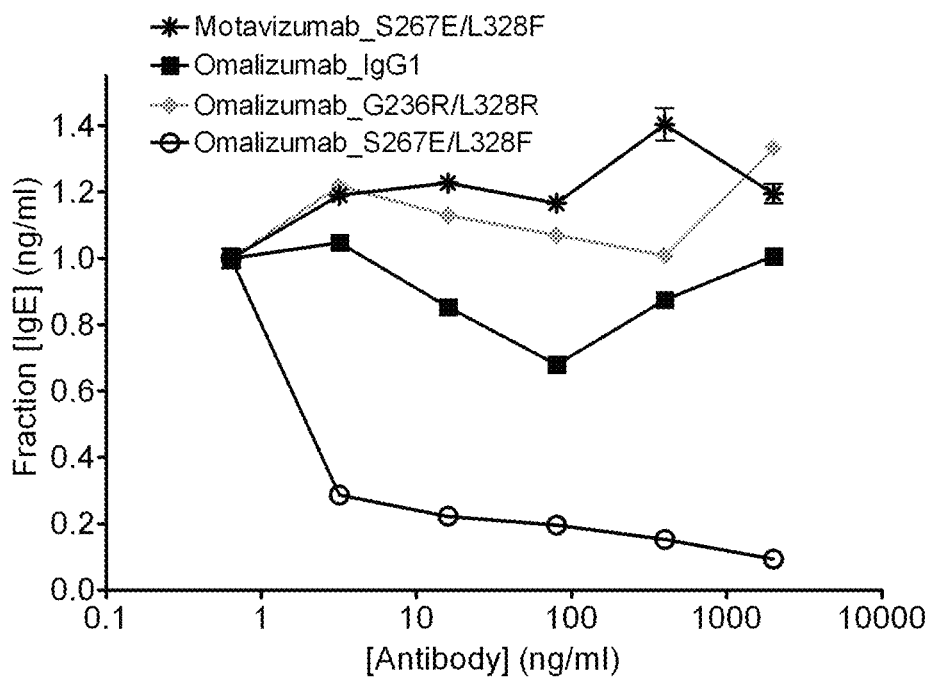
FIG. 16. Inhibition of class-switched IgE+ B cells with variant anti-IgE antibodies enhanced for FcγRIIb affinity. The plot shows the concentration of IgE released from PBMCs after 14 days incubation with IL-4, anti-CD40 (α-CD40) agonist antibody, anti-mu BCR cross-linking antibody, and varying concentrations of the antibodies shown. Data were normalized to the lowest concentration of antibody.

The capacity of anti-IgE antibodies with high FcγRIIb affinity to inhibit IgE production was evaluated in the presence of mIgE BCR stimulation. The above assay was repeated, with class-switching to IgE promoted by IL-4 and α-CD40 agonist antibody, and in addition the B cells were activated using either anti-mu or anti-CD79b antibody. These antibodies cross-link the BCR, thereby providing a signal similar to immune-complexed antigen. Anti-mu antibody cross-links membrane-anchored IgM, and anti-CD79b cross-links CD79b, which is a signaling component of the BCR complex. PBMCs were incubated for 14 days with IL-4, α-CD40, and either anti-CD79b or anti-mu, and IgE was detected as described above. The results for anti-CD79b (FIG. 15) and anti-mu (FIG. 16) show that the anti-IgE antibodies with high affinity for FcγRIIb are capable of inhibiting IgE production when B cells are stimulated via BCR cross-linking.

Figure 17:
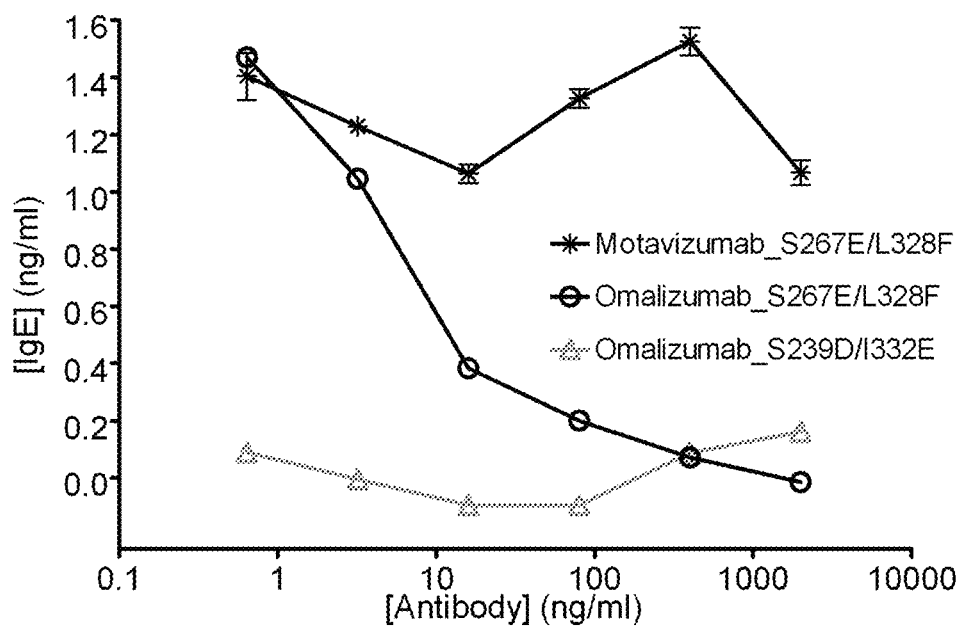
FIG. 17. Inhibition of class-switched IgE+ B cells with variant anti-IgE antibodies enhanced ADCC and ADCP effector function. The plot shows the concentration of IgE released from PBMCs after 14 days incubation with IL-4, anti-CD40 (α-CD40) agonist antibody, anti-CD79b BCR cross-linking antibody, and varying concentrations of the antibodies shown.
Figure 18:
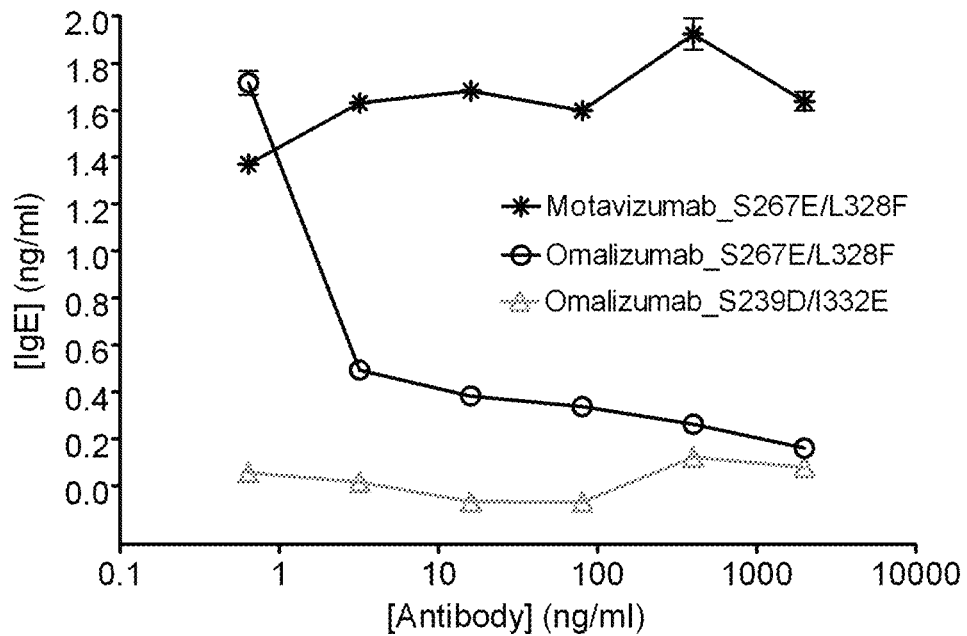
FIG. 18. Inhibition of class-switched IgE+ B cells with variant anti-IgE antibodies enhanced ADCC and ADCP effector function. The plot shows the concentration of IgE released from PBMCs after 14 days incubation with IL-4, anti-CD40 (α-CD40) agonist antibody, anti-mu BCR cross-linking antibody, and varying concentrations of the antibodies shown.
Figure 19:
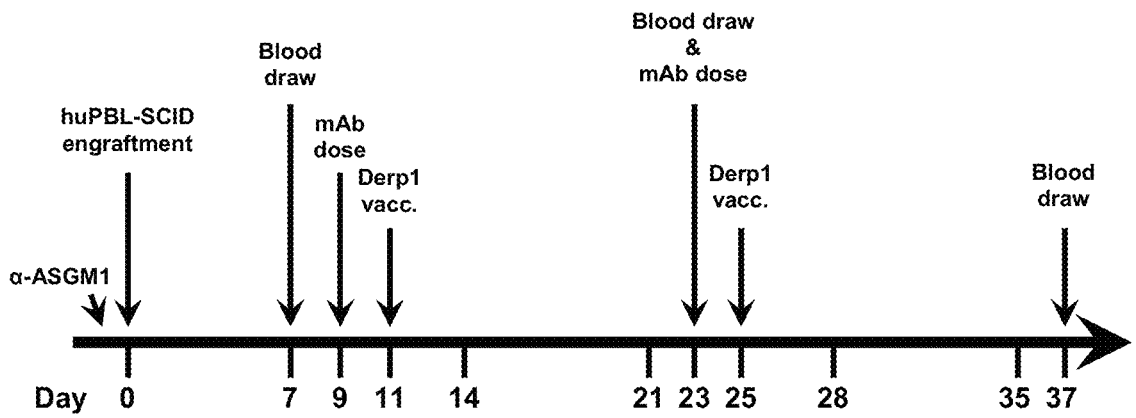
FIG. 19. Protocol for huPBL-SCID in vivo study to test activity of anti-IgE antibodies. The indicated days reflect the number of days after engraftment of PBMCs from a donor testing positive for IgE antibodies specific for Der p 1. Derp1 vacc. indicates vaccination with Der p 1 antigen.

An additional strategy for inhibiting IgE+ B cells is to deplete them. This may be carried out using an anti-IgE antibody that is enhanced for effector function. The variant S239D/I332E increases binding to activating receptor FcγRIIa and FcγRIIIa (FIG. 3 and FIG. 4), and thus improves ADCC and ADCP effector functions. The above B cell assay was carried out using a S239D/I332E variant of the anti-IgE antibody Omalizumab. PBMCs were incubated for 14 days with IL-4, α-CD40, and either anti-CD79b (FIG. 17) or anti-mu (FIG. 18), and IgE was detected as described above. The results (FIGS. 17 and 18) show that anti-IgE antibodies with optimized effector function are able to inhibit IgE production from class-switched IgE+ B cells.

Example 4

In Vivo Inhibition of IgE+ B Cells by Anti-IgE Antibodies with High Affinity to FcγRIIb The immunoglobulins disclosed herein were assessed using a huPBL-SCID mouse model as a proxy for therapeutic activity in humans. This study examined the capacity of the anti-IgE antibodies described here to inhibit B cell activity and plasma cell development in response to a common human allergen—dust mite protein Der p 1. In this method, human peripheral blood leukocytes (PBLs) from a blood donor with allergic response to Der p 1 were engrafted to immune-deficient SCID mice and treated with the native or variant anti-IgE antibodies. The mice were challenged with an antigen to stimulate an immune response, and production of immunoglobulins was measured to examine the course of B cell development into plasma cells.

Blood donors were screened for allergy to dust mite antigen based on the presence of anti-IgE antibodies against Der p 1. A donor with positive reactivity was leukapheresed to obtained peripheral blood mononuclear cells (PBMCs). The protocol for the study is provided in FIG. 20. One day prior to PBMC injection, mice were given intraperitoneal (i.p.) injections with 100 ul of anti-asialo GM antibody (Wako, Richmond, Va.) to deplete murine natural killer (NK) cells. The next day, mice were injected i.p. with $3 \times 10^7$ PBLs in a 0.5 ml volume. After PBMC injection, mice were assigned to 5 different groups of mice with 7 mice in each group. On day 7 post PBMC injection, blood was collected from all mice via retro-orbital sinus/plexus (OSP) puncture for determination of human IgG and IgE levels by ELISA (ZeptoMetrix, Buffalo, N.Y.). Two days later (day 9), mice were injected i.p. with 10 mg/kg antibody or PBS. On day 11, mice were injected i.p. with 15 ug dustmite antigen Der p 1 (LoTox Natural Der p 1, Indoor Biotechnologies, Charlottesville, Va.). On day 23 (12 days post antigen vaccination), blood was collected from all mice for determination of human IgG and IgE antibodies. On the same day, mice received a second injection i.p. with 10 mg/kg antibody or PBS. Two days later (day 25), mice received a boost vaccination i.p. of 10 ug dustmite antigen Der p 1. On day 37 (12 days post antigen boost), blood was collected by OSP for human immunoglobulin determination. Human IgG and IgE concentrations were measured using ELISA methods similar to those described above.

Figure 20:
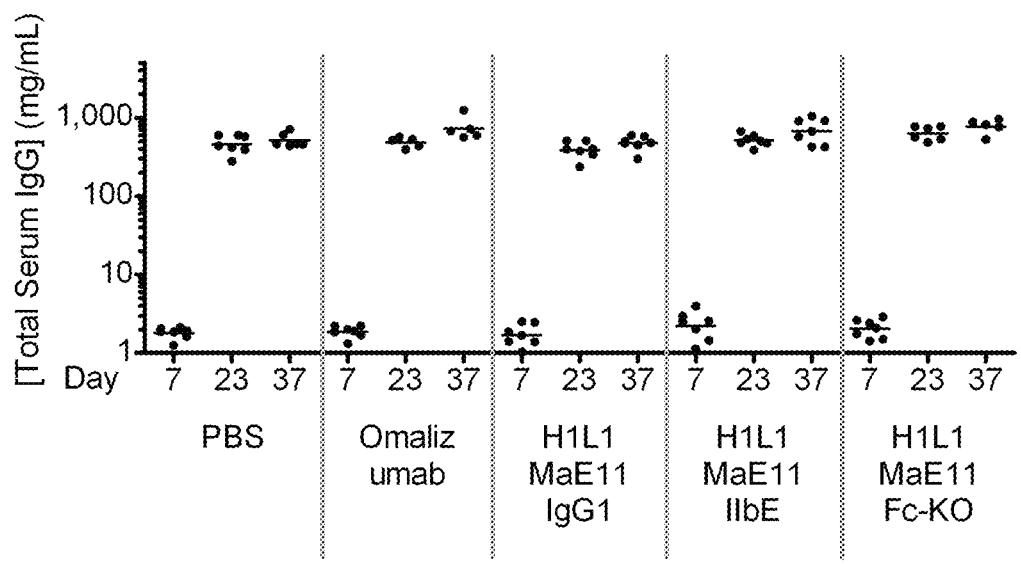
FIG. 20. Total serum IgG levels from the huPBL-SCID in vivo model for each treatment group. The indicated days (7, 23, and 37) reflect the blood draws outlined in the protocol in FIG. 19. PBS indicates the untreated vehicle group, Omalizumab indicates the group treated with Omalizumab_IgG1, and the 3 H1L1 MaE11 groups indicate groups treated with humanized MaE11 comprising either a WT IgG1 (IgG1), S267E/L328F variant (IIbE), or G236R/L328R (Fc-KO) Fc region.
Figure 21:
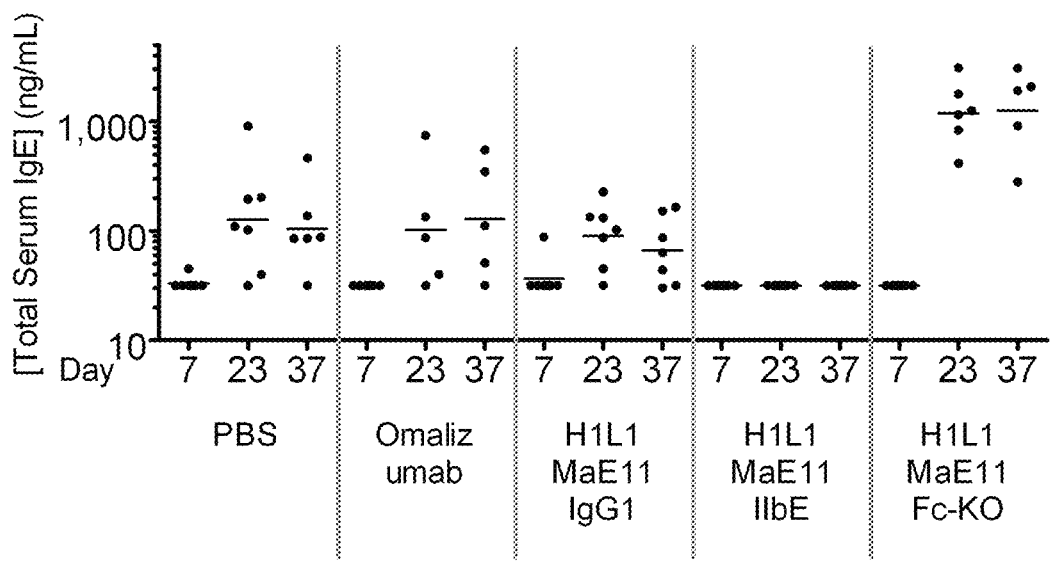
FIG. 21. Total serum IgE levels from the huPBL-SCID in vivo model for each treatment group. The indicated days (7, 23, and 37) reflect the blood draws outlined in the protocol in FIG. 19. PBS indicates the untreated vehicle group, Omalizumab indicates the group treated with Omalizumab_IgG1, and the 3 H1L1 MaE11 groups indicate groups treated with humanized MaE11 comprising either a WT IgG1 (IgG1), S267E/L328F variant (IIbE), or G236R/L328R (Fc-KO) Fc region. The limit of quantitation for the ELISA method was 31.6 ng/mL; samples that were below this limit were reported as 31.6 ng/mL in the plot.

The results are shown in FIGS. 20 and 21 for serum IgG and IgE levels respectively. Before the allergen challenge, the levels of human IgG and IgE antibodies were low in all the groups. After Der p 1 immunization, all groups showed high levels of human IgG, indicating a robust immune response by engrafted human B cells to either the vaccinated Der p 1 antigen or endogenous mouse antigens. In contrast to IgG response, the treatment groups differed significantly in their production of IgE antibodies. Omalizumab and the IgG1 version of H1 L1 MaE11 were equivalent to vehicle in their capacity to inhibit production of human IgE. However the FcγRIIb-enhanced (IIbE, S267E/L328F) version of H1L1 MaE11 showed no detectable levels of human IgE. The Fc-KO (variant G236R/L328R) version of H1L1 MaE11, which lacks binding to all FcγRs, showed an enhancement in human IgE production. This is possibly due to its ability to cross-link human mIgE and thus activate IgE+ B cells, yet its complete lack of FcγRIIb inhibitory or FcγRIIa/IIIa cytotoxic activities such as those possessed by the IgG1 and IIbE versions of the antibody. These in vivo data show that anti-IgE antibodies with high affinity for FcγRIIb are capable of inhibiting human IgE+ B cell activation and immunoglobulin secreting plasma cell differentiation, and thus support the potential of the immunoglobulins disclosed herein for treating IgE-mediated disorders.

All cited references are herein expressly incorporated by reference in their entirety.

Whereas particular embodiments have been described above for purposes of illustration, it will be appreciated by those skilled in the art that numerous variations of the details may be made without departing from the invention as described in the appended claims.

We claim:

1. A method of treating allergic asthma in a patient comprising administering to said patient an anti-IgE antibody comprising a heavy chain having SEQ ID NO:42 and a light chain having SEQ ID NO:40.

* * * * *

SEQUENCE LISTING

```
<160> NUMBER OF SEQ ID NOS: 45

<210> SEQ ID NO 1
<211> LENGTH: 121
<212> TYPE: PRT
<213> ORGANISM: Artificial Sequence
<220> FEATURE:
<223> OTHER INFORMATION: Omalizumab VH Humanized

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser
        115                 120

<210> SEQ ID NO 2
<211> LENGTH: 9
<212> TYPE: PRT
<213> ORGANISM: Mus musculus

<400> SEQUENCE: 2

Tyr Ser Ile Thr Ser Gly Tyr Ser Trp
1               5
```

```
<210> SEQ ID NO 3
<211> LENGTH: 5
<212> TYPE: PRT
<213> ORGANISM: Mus musculus

<400> SEQUENCE: 3

Thr Tyr Asp Gly Ser
1               5

<210> SEQ ID NO 4
<211> LENGTH: 12
<212> TYPE: PRT
<213> ORGANISM: Mus musculus

<400> SEQUENCE: 4

Gly Ser His Tyr Phe Gly His Trp His Phe Ala Val
1               5                   10

<210> SEQ ID NO 5
<211> LENGTH: 111
<212> TYPE: PRT
<213> ORGANISM: Artificial Sequence
<220> FEATURE:
<223> OTHER INFORMATION: Omalizumab VL Humanized

<400> SEQUENCE: 5

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110

<210> SEQ ID NO 6
<211> LENGTH: 10
<212> TYPE: PRT
<213> ORGANISM: Mus musculus

<400> SEQUENCE: 6

Gln Ser Val Asp Tyr Asp Gly Asp Ser Tyr
1               5                   10

<210> SEQ ID NO 7
<211> LENGTH: 7
<212> TYPE: PRT
<213> ORGANISM: Mus musculus

<400> SEQUENCE: 7

Ala Ala Ser Tyr Leu Glu Ser
1               5

<210> SEQ ID NO 8
<211> LENGTH: 7
<212> TYPE: PRT
```

```
<213> ORGANISM: Mus musculus

<400> SEQUENCE: 8

Ser His Glu Asp Pro Tyr Thr
1               5

<210> SEQ ID NO 9
<211> LENGTH: 121
<212> TYPE: PRT
<213> ORGANISM: Mus musculus

<400> SEQUENCE: 9

Asp Val Gln Leu Gln Glu Ser Gly Pro Gly Leu Val Lys Pro Ser Gln
1               5                   10                  15

Ser Leu Ser Leu Ala Cys Ser Val Thr Gly Tyr Ser Ile Thr Ser Gly
            20                  25                  30

Tyr Ser Trp Asn Trp Ile Arg Gln Phe Pro Gly Asn Lys Leu Glu Trp
        35                  40                  45

Met Gly Ser Ile Thr Tyr Asp Gly Ser Ser Asn Tyr Asn Pro Ser Leu
    50                  55                  60

Lys Asn Arg Ile Ser Val Thr Arg Asp Thr Ser Gln Asn Gln Phe Phe
65                  70                  75                  80

Leu Lys Leu Asn Ser Ala Thr Ala Glu Asp Thr Ala Thr Tyr Tyr Cys
                85                  90                  95

Ala Arg Gly Ser His Tyr Phe Gly His Trp His Phe Ala Val Trp Gly
            100                 105                 110

Ala Gly Thr Thr Val Thr Val Ser Ser
        115                 120

<210> SEQ ID NO 10
<211> LENGTH: 9
<212> TYPE: PRT
<213> ORGANISM: Mus musculus

<400> SEQUENCE: 10

Tyr Ser Ile Thr Ser Gly Tyr Ser Trp
1               5

<210> SEQ ID NO 11
<211> LENGTH: 5
<212> TYPE: PRT
<213> ORGANISM: Mus musculus

<400> SEQUENCE: 11

Thr Tyr Asp Gly Ser
1               5

<210> SEQ ID NO 12
<211> LENGTH: 12
<212> TYPE: PRT
<213> ORGANISM: Mus musculus

<400> SEQUENCE: 12

Gly Ser His Tyr Phe Gly His Trp His Phe Ala Val
1               5                   10

<210> SEQ ID NO 13
<211> LENGTH: 111
<212> TYPE: PRT
<213> ORGANISM: Mus musculus

<400> SEQUENCE: 13
```

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Ile Leu Leu Ile Tyr Ala Ala Ser Tyr Leu Gly Ser Glu Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Phe Tyr Cys Gln Gln Ser His
                85                  90                  95

Glu Asp Pro Tyr Thr Phe Gly Ala Gly Thr Lys Leu Glu Ile Lys
            100                 105                 110

<210> SEQ ID NO 14
<211> LENGTH: 10
<212> TYPE: PRT
<213> ORGANISM: Mus musculus

<400> SEQUENCE: 14

Gln Ser Val Asp Tyr Asp Gly Asp Ser Tyr
1               5                   10

<210> SEQ ID NO 15
<211> LENGTH: 7
<212> TYPE: PRT
<213> ORGANISM: Mus musculus

<400> SEQUENCE: 15

Ala Ala Ser Tyr Leu Gly Ser
1               5

<210> SEQ ID NO 16
<211> LENGTH: 7
<212> TYPE: PRT
<213> ORGANISM: Mus musculus

<400> SEQUENCE: 16

Ser His Glu Asp Pro Tyr Thr
1               5

<210> SEQ ID NO 17
<211> LENGTH: 121
<212> TYPE: PRT
<213> ORGANISM: Artificial Sequence
<220> FEATURE:
<223> OTHER INFORMATION: H1L1MaE11 VH Humanized

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Ser Trp Asn Trp Ile Arg Gln Pro Pro Gly Lys Leu Glu Trp
        35                  40                  45

Ile Gly Ser Ile Thr Tyr Asp Gly Ser Ser Asn Tyr Asn Pro Ser Leu
50                  55                  60

Lys Ser Arg Val Thr Ile Ser Arg Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Gly Ser His Tyr Phe Gly His Trp His Phe Ala Val Trp Gly
            100                 105                 110

Ala Gly Thr Leu Val Thr Val Ser Ser
        115                 120

<210> SEQ ID NO 18
<211> LENGTH: 9
<212> TYPE: PRT
<213> ORGANISM: Mus musculus

<400> SEQUENCE: 18

Tyr Ser Ile Thr Ser Gly Tyr Ser Trp
1               5

<210> SEQ ID NO 19
<211> LENGTH: 5
<212> TYPE: PRT
<213> ORGANISM: Mus musculus

<400> SEQUENCE: 19

Thr Tyr Asp Gly Ser
1               5

<210> SEQ ID NO 20
<211> LENGTH: 12
<212> TYPE: PRT
<213> ORGANISM: Mus musculus

<400> SEQUENCE: 20

Gly Ser His Tyr Phe Gly His Trp His Phe Ala Val
1               5                   10

<210> SEQ ID NO 21
<211> LENGTH: 111
<212> TYPE: PRT
<213> ORGANISM: Mus musculus

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Tyr Leu Gly Ser Glu Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Ala Gly Thr Lys Leu Glu Ile Lys
            100                 105                 110

<210> SEQ ID NO 22
<211> LENGTH: 10
<212> TYPE: PRT
<213> ORGANISM: Mus musculus

<400> SEQUENCE: 22
```

Gln Ser Val Asp Tyr Asp Gly Asp Ser Tyr
1               5                   10

<210> SEQ ID NO 23
<211> LENGTH: 7
<212> TYPE: PRT
<213> ORGANISM: Mus musculus

<400> SEQUENCE: 23

Ala Ala Ser Tyr Leu Gly Ser
1               5

<210> SEQ ID NO 24
<211> LENGTH: 7
<212> TYPE: PRT
<213> ORGANISM: Mus musculus

<400> SEQUENCE: 24

Ser His Glu Asp Pro Tyr Thr
1               5

<210> SEQ ID NO 25
<211> LENGTH: 123
<212> TYPE: PRT
<213> ORGANISM: Mus musculus

<400> SEQUENCE: 25

Gln Val Gln Leu Gln Gln Ser Gly Ala Glu Leu Met Lys Pro Gly Ala
1               5                   10                  15

Ser Val Lys Ile Ser Cys Lys Thr Thr Gly Tyr Thr Phe Ser Met Tyr
                20                  25                  30

Trp Leu Glu Trp Val Lys Gln Arg Pro Gly His Gly Leu Glu Trp Val
            35                  40                  45

Gly Glu Ile Ser Pro Gly Thr Phe Thr Thr Asn Tyr Asn Glu Lys Phe
        50                  55                  60

Lys Ala Lys Ala Thr Phe Thr Ala Asp Thr Ser Ser Asn Thr Ala Tyr
65                  70                  75                  80

Leu Gln Leu Ser Gly Leu Thr Ser Glu Asp Ser Ala Val Tyr Phe Cys
                85                  90                  95

Ala Arg Phe Ser His Phe Ser Gly Ser Asn Tyr Asp Tyr Phe Asp Tyr
            100                 105                 110

Trp Gly Gln Gly Thr Ser Leu Thr Val Ser Ser
        115                 120

<210> SEQ ID NO 26
<211> LENGTH: 7
<212> TYPE: PRT
<213> ORGANISM: Mus musculus

<400> SEQUENCE: 26

Tyr Thr Phe Ser Met Tyr Trp
1               5

<210> SEQ ID NO 27
<211> LENGTH: 6
<212> TYPE: PRT
<213> ORGANISM: Mus musculus

<400> SEQUENCE: 27

Ser Pro Gly Thr Phe Thr
1               5

```
<210> SEQ ID NO 28
<211> LENGTH: 14
<212> TYPE: PRT
<213> ORGANISM: Mus musculus

<400> SEQUENCE: 28

Phe Ser His Phe Ser Gly Ser Asn Tyr Asp Tyr Phe Asp Tyr
1               5                   10

<210> SEQ ID NO 29
<211> LENGTH: 107
<212> TYPE: PRT
<213> ORGANISM: Mus musculus

<400> SEQUENCE: 29

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asp Gly Ser Pro Arg Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Glu Phe Thr Leu Asn Ile Asn Ser Val Glu Ser
65                  70                  75                  80

Glu Asp Ile Ala Asp Tyr Tyr Cys Gln Gln Ser Asp Ser Trp Pro Thr
                85                  90                  95

Thr Phe Gly Gly Gly Thr Lys Leu Glu Ile Lys
            100                 105

<210> SEQ ID NO 30
<211> LENGTH: 6
<212> TYPE: PRT
<213> ORGANISM: Mus musculus

<400> SEQUENCE: 30

Gln Ser Ile Gly Thr Asn
1               5

<210> SEQ ID NO 31
<211> LENGTH: 7
<212> TYPE: PRT
<213> ORGANISM: Mus musculus

<400> SEQUENCE: 31

Tyr Ala Ser Glu Ser Ile Ser
1               5

<210> SEQ ID NO 32
<211> LENGTH: 7
<212> TYPE: PRT
<213> ORGANISM: Mus musculus

<400> SEQUENCE: 32

Ser Asp Ser Trp Pro Thr Thr
1               5

<210> SEQ ID NO 33
<211> LENGTH: 107
<212> TYPE: PRT
<213> ORGANISM: Mus musculus
```

<400> SEQUENCE: 33

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 34
<211> LENGTH: 330
<212> TYPE: PRT
<213> ORGANISM: Mus musculus

<400> SEQUENCE: 34

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 35
<211> LENGTH: 330
<212> TYPE: PRT
<213> ORGANISM: Artificial Sequence
<220> FEATURE:
<223> OTHER INFORMATION: S267E/L328F IgG1 constant chain Artificial
      Variant

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 330
<212> TYPE: PRT
<213> ORGANISM: Artificial Sequence
<220> FEATURE:
<223> OTHER INFORMATION: G236D/S267E IgG1 constant chain Artificial
      Variant

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Asp Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 218
<212> TYPE: PRT
<213> ORGANISM: Artificial Sequence
<220> FEATURE:
<223> OTHER INFORMATION: Omalizumab light chain (VH-C ) Artificial
      Variant

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 38
<211> LENGTH: 451
<212> TYPE: PRT
<213> ORGANISM: Artificial Sequence
<220> FEATURE:
<223> OTHER INFORMATION: Omalizumab IgG1 heavy chain Artificial Variant

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
```

```
            50                  55                  60
Lys Gly Arg Ile Thr Ile Ser Arg Asp Asp Ser Lys Asn Thr Phe Tyr
 65                  70                  75                  80

Leu Gln Met Asn Ser Leu Arg Ala Glu Asp Thr Ala Val Tyr Tyr Cys
                 85                  90                  95

Ala Arg Gly Ser His Tyr Phe Gly His Trp His Phe Ala Val Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 39
```

```
<211> LENGTH: 451
<212> TYPE: PRT
<213> ORGANISM: Artificial Sequence
<220> FEATURE:
<223> OTHER INFORMATION: Omalizumab S267E/L328F heavy chain Artificial
      Humanized

<400> SEQUENCE: 39
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Val | Ser | Gly | Tyr | Ser | Ile | Thr | Ser | Gly |
|---|---|---|---|---|---|---|---|---|---|---|---|---|---|---|---|
| | | | 20 | | | | | 25 | | | | | 30 | | |

| Tyr | Ser | Trp | Asn | Trp | Ile | Arg | Gln | Ala | Pro | Gly | Lys | Gly | Leu | Glu | Trp |
|---|---|---|---|---|---|---|---|---|---|---|---|---|---|---|---|
| | | 35 | | | | | 40 | | | | | 45 | | | |

| Val | Ala | Ser | Ile | Thr | Tyr | Asp | Gly | Ser | Thr | Asn | Tyr | Asn | Pro | Ser | Val |
|---|---|---|---|---|---|---|---|---|---|---|---|---|---|---|---|
| 50 | | | | | 55 | | | | | 60 | | | | | |

| Lys | Gly | Arg | Ile | Thr | Ile | Ser | Arg | Asp | Asp | Ser | Lys | Asn | Thr | Phe | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Ser | His | Tyr | Phe | Gly | His | Trp | His | Phe | Ala | Val | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ser | Ala | Ser | Thr | Lys | Gly | Pro | Ser |
|---|---|---|---|---|---|---|---|---|---|---|---|---|---|---|---|
| | | 115 | | | | | 120 | | | | | 125 | | | |

| Val | Phe | Pro | Leu | Ala | Pro | Ser | Ser | Lys | Ser | Thr | Ser | Gly | Gly | Thr | Ala |
|---|---|---|---|---|---|---|---|---|---|---|---|---|---|---|---|
| | 130 | | | | | 135 | | | | | 140 | | | | |

| Ala | Leu | Gly | Cys | Leu | Val | Lys | Asp | Tyr | Phe | Pro | Glu | Pro | Val | Thr | Val |
|---|---|---|---|---|---|---|---|---|---|---|---|---|---|---|---|
| 145 | | | | | 150 | | | | | 155 | | | | | 160 |

| Ser | Trp | Asn | Ser | Gly | Ala | Leu | Thr | Ser | Gly | Val | His | Thr | Phe | Pro | Ala |
|---|---|---|---|---|---|---|---|---|---|---|---|---|---|---|---|
| | | | | 165 | | | | | 170 | | | | | 175 | |

| Val | Leu | Gln | Ser | Ser | Gly | Leu | Tyr | Ser | Leu | Ser | Ser | Val | Val | Thr | Val |
|---|---|---|---|---|---|---|---|---|---|---|---|---|---|---|---|
| | | | 180 | | | | | 185 | | | | | 190 | | |

| Pro | Ser | Ser | Ser | Leu | Gly | Thr | Gln | Thr | Tyr | Ile | Cys | Asn | Val | Asn | His |
|---|---|---|---|---|---|---|---|---|---|---|---|---|---|---|---|
| | | 195 | | | | | 200 | | | | | 205 | | | |

| Lys | Pro | Ser | Asn | Thr | Lys | Val | Asp | Lys | Lys | Val | Glu | Pro | Lys | Ser | Cys |
|---|---|---|---|---|---|---|---|---|---|---|---|---|---|---|---|
| | 210 | | | | | 215 | | | | | 220 | | | | |

| Asp | Lys | Thr | His | Thr | Cys | Pro | Pro | Cys | Pro | Ala | Pro | Glu | Leu | Leu | Gly |
|---|---|---|---|---|---|---|---|---|---|---|---|---|---|---|---|
| 225 | | | | | 230 | | | | | 235 | | | | | 240 |

| Gly | Pro | Ser | Val | Phe | Leu | Phe | Pro | Pro | Lys | Pro | Lys | Asp | Thr | Leu | Met |
|---|---|---|---|---|---|---|---|---|---|---|---|---|---|---|---|
| | | | | 245 | | | | | 250 | | | | | 255 | |

| Ile | Ser | Arg | Thr | Pro | Glu | Val | Thr | Cys | Val | Val | Val | Asp | Val | Glu | His |
|---|---|---|---|---|---|---|---|---|---|---|---|---|---|---|---|
| | | | 260 | | | | | 265 | | | | | 270 | | |

| Glu | Asp | Pro | Glu | Val | Lys | Phe | Asn | Trp | Tyr | Val | Asp | Gly | Val | Glu | Val |
|---|---|---|---|---|---|---|---|---|---|---|---|---|---|---|---|
| | | 275 | | | | | 280 | | | | | 285 | | | |

| His | Asn | Ala | Lys | Thr | Lys | Pro | Arg | Glu | Glu | Gln | Tyr | Asn | Ser | Thr | Tyr |
|---|---|---|---|---|---|---|---|---|---|---|---|---|---|---|---|
| | 290 | | | | | 295 | | | | | 300 | | | | |

| Arg | Val | Val | Ser | Val | Leu | Thr | Val | Leu | His | Gln | Asp | Trp | Leu | Asn | Gly |
|---|---|---|---|---|---|---|---|---|---|---|---|---|---|---|---|
| 305 | | | | | 310 | | | | | 315 | | | | | 320 |

| Lys | Glu | Tyr | Lys | Cys | Lys | Val | Ser | Asn | Lys | Ala | Phe | Pro | Ala | Pro | Ile |
|---|---|---|---|---|---|---|---|---|---|---|---|---|---|---|---|
| | | | | 325 | | | | | 330 | | | | | 335 | |

| Glu | Lys | Thr | Ile | Ser | Lys | Ala | Lys | Gly | Gln | Pro | Arg | Glu | Pro | Gln | Val |
|---|---|---|---|---|---|---|---|---|---|---|---|---|---|---|---|
| | | | 340 | | | | | 345 | | | | | 350 | | |

| Tyr | Thr | Leu | Pro | Pro | Ser | Arg | Glu | Glu | Met | Thr | Lys | Asn | Gln | Val | Ser |
|---|---|---|---|---|---|---|---|---|---|---|---|---|---|---|---|
| | | 355 | | | | | 360 | | | | | 365 | | | |

| Leu | Thr | Cys | Leu | Val | Lys | Gly | Phe | Tyr | Pro | Ser | Asp | Ile | Ala | Val | Glu |

```
                  370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 40
<211> LENGTH: 218
<212> TYPE: PRT
<213> ORGANISM: Artificial Sequence
<220> FEATURE:
<223> OTHER INFORMATION: H1L1 MaE11 light chain (VH-C ) Artificial
      Humanized

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Tyr Leu Gly Ser Glu Ile Pro Ala
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Ala Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 41
<211> LENGTH: 451
<212> TYPE: PRT
<213> ORGANISM: Artificial Sequence
<220> FEATURE:
<223> OTHER INFORMATION: H1L1 MaE11 IgG1 heavy chain Artificial
      Humanized
```

```
<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Ser Trp Asn Trp Ile Arg Gln Pro Pro Gly Lys Lys Leu Glu Trp
        35                  40                  45

Ile Gly Ser Ile Thr Tyr Asp Gly Ser Asn Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser His Tyr Phe Gly His Trp His Phe Ala Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 42
<211> LENGTH: 451
<212> TYPE: PRT
<213> ORGANISM: Artificial Sequence
<220> FEATURE:
<223> OTHER INFORMATION: H1L1 MaE11 S267E/L328F heavy chain Artificial
      Humanized

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Ser Trp Asn Trp Ile Arg Gln Pro Pro Gly Lys Lys Leu Glu Trp
        35                  40                  45

Ile Gly Ser Ile Thr Tyr Asp Gly Ser Ser Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser His Tyr Phe Gly His Trp His Phe Ala Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly

```
              305                 310                 315                 320
Lys Glu Tyr Lys Cys Lys Val Ser Asn Lys Ala Phe Pro Ala Pro Ile
                    325                 330                 335

Glu Lys Thr Ile Ser Lys Ala Lys Gly Gln Pro Arg Glu Pro Gln Val
                    340                 345                 350

Tyr Thr Leu Pro Pro Ser Arg Glu Glu Met Thr Lys Asn Gln Val Ser
                    355                 360                 365

Leu Thr Cys Leu Val Lys Gly Phe Tyr Pro Ser Asp Ile Ala Val Glu
                    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
    450

<210> SEQ ID NO 43
<211> LENGTH: 5
<212> TYPE: DNA
<213> ORGANISM: Artificial Sequence
<220> FEATURE:
<223> OTHER INFORMATION: glycine-serine linker

<400> SEQUENCE: 43 gsggs                                                                   5

<210> SEQ ID NO 44
<211> LENGTH: 5
<212> TYPE: DNA
<213> ORGANISM: Artificial Sequence
<220> FEATURE:
<223> OTHER INFORMATION: glycine-serine linker

<400> SEQUENCE: 44 ggggs                                                                   5

<210> SEQ ID NO 45
<211> LENGTH: 4
<212> TYPE: DNA
<213> ORGANISM: Artificial Sequence
<220> FEATURE:
<223> OTHER INFORMATION: glycine-serine linker

<400> SEQUENCE: 45 gggs                                                                    4
```